United States Patent [19]
Reed

[11] Patent Number: 5,879,687
[45] Date of Patent: Mar. 9, 1999

[54] METHODS FOR ENHANCEMENT OF PROTECTIVE IMMUNE RESPONSES

[75] Inventor: Steven G. Reed, Bellevue, Wash.

[73] Assignee: Corixa Corporation, Seattle, Wash.

[21] Appl. No.: 634,642

[22] Filed: Apr. 18, 1996

Related U.S. Application Data

[63] Continuation-in-part of Ser. No. 607,509, Feb. 23, 1996, which is a continuation-in-part of Ser. No. 488,386, Jun. 6, 1995, abandoned, which is a continuation-in-part of Ser. No. 232,534, Apr. 22, 1994, abandoned.

[51] Int. Cl.$^6$ ........................ A61K 39/008; A61K 39/39; C07K 14/44; C12N 15/30
[52] U.S. Cl. .................................. 424/269.1; 424/184.1; 514/12
[58] Field of Search .............................. 424/184.1, 269.1; 514/12

[56] References Cited

U.S. PATENT DOCUMENTS

| | | |
|---|---|---|
| 5,304,371 | 4/1994 | Reed . |
| 5,413,912 | 5/1995 | Reed . |
| 5,543,143 | 8/1996 | Reed . |

FOREIGN PATENT DOCUMENTS

| | | |
|---|---|---|
| 9529239 | 11/1995 | WIPO . |
| 9639524 | 12/1996 | WIPO . |

OTHER PUBLICATIONS

Kim et al Nucleic Acid Res. vol. 21 No. 8 pp. 2012, 1993.
Probst et al Eur J. Immunol 27:2634–2642, 1997.
Metz et al, Gene 131:299–300, 1993.
Carvalho et al J. Immunol. 152:5949–5956, 1994.
Y.A.W. Skeiky et al., "Proliferative and Cytokine Responses of Human PBMC to Cloned *Leishmania braziliensis* Heat Shock and Ribosomal Antigens," *Journal of Immunology* 150(8): 93a, 1993.
S.L. Reiner et al., "Leishmania Promastigotes Evade Interleukin 12 (IL–12) Induction by Macrophages and Stimulate a Broad Range of Cytokines from CD4$^+$T Cells During Initiation of Infection," *J. Exp. Med.* 179(2): 447–456, 1994.
F.P. Heinzel et al., "Recombinant Interleukin 12 Cures Mice Infected with *Leishmania major*," *J. Exp. Med.* 177(5): 1505–1509, 1993.
J.P. Sypek et al., "Resolution of Cutaneous Leishmaniasis: Interleukin 12 Initiates a Protective T Helper Type 1 Immune Response," *J. Exp. Med.* 177(6): 1797–1802, 1993.
L.C.C. Afonso et al., "The Adjuvant Effect of Interleukin–12 in a Vaccine Against *Leishmania major*," *Science* 263: 235–237, 1994.
Reed and Scott, "T–Cell and cytokine responses in leishmaniasis," *Current Opinion in Immunology* 5(4): 524–531, 1993.
Y.A.W. Skeiky et al., "A Recombinant Leishmania Antigen that Stimulates Human Peripheral Blood Mononuclear Cells to Express a Th1–Type Cytokine Profile and to Produce Interleukin 12," *J. Exp. Med.* 181: 1527–1537, 1995.
G. Trinchieri, "Interleukin–12 and its role in the generation of $T_H1$ cells," *Immunology Today* 14(7): 335–338, 1993.
Ghalib et al., "IL–12 Enhances Th1–Type Responses in Human *Leishmania donovani* Infections," *J. Immunol.* 154(9): 4623–4629, 1995.

*Primary Examiner*—Nita Minnifield
*Attorney, Agent, or Firm*—Seed & Berry LLP

[57] ABSTRACT

Methods for eliciting or enhancing immune responses to antigens, including tumor antigens, and/or DNA vaccines are provided. The methods employ polypeptides or nucleic acid compositions that contain at least a biologically active portion of a *Leishmania braziliensis* or *Leishmania major* homologue of the eukaryotic initiation factor 4A, or a variant thereof. Such polypeptides and compositions are useful for enhancing or eliciting a patient's cellular and/or humoral immune response, for instance within methods for treating tumors.

10 Claims, 19 Drawing Sheets

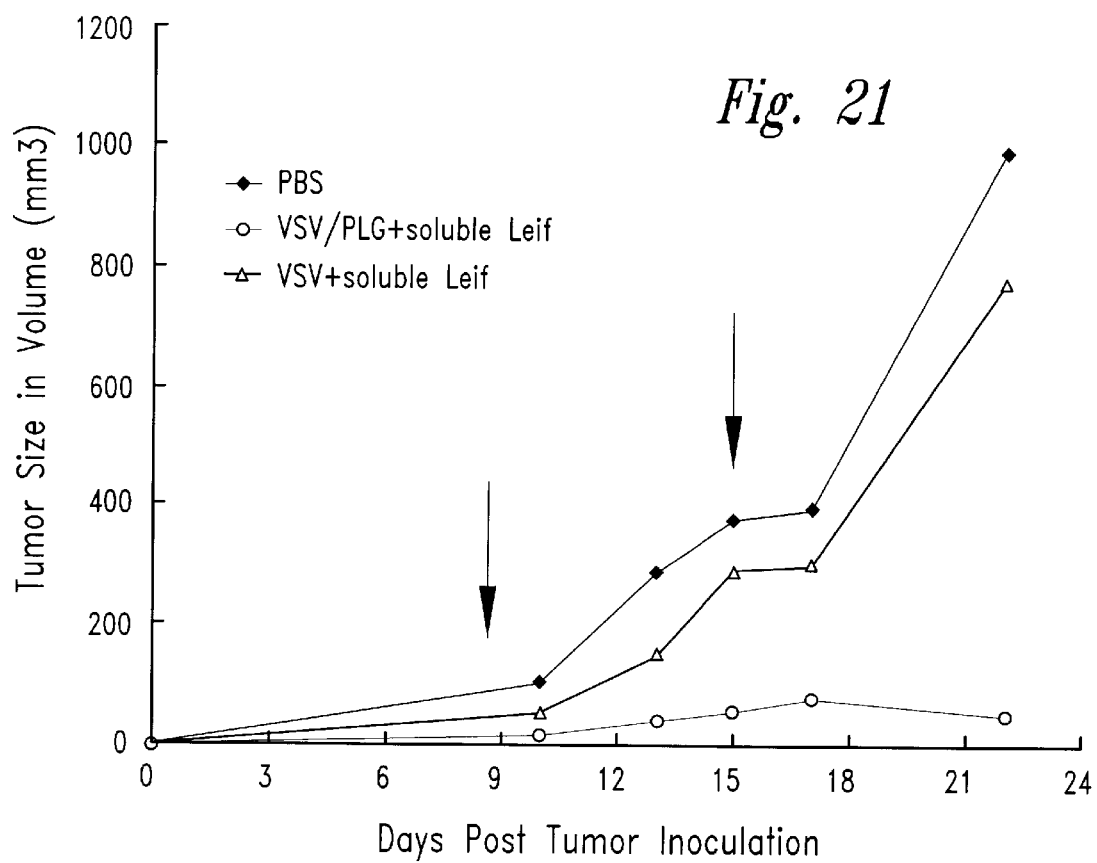

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 1618 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 115..1326

( x i ) SEQUENCE DESCRIPTION: SEQ ID NO:1:

```
CCACTCTCTC  GGTCGTCTGT  CTCCCACGCG  CGCACGCAGT  TGATTTCCGC  CTTCTTAAAC         60

GCTCTCTTTT  TTTTTATTTT  TCACCTGACC  AACCGCACCA  CGTCGGCCTC  CATC ATG          117
                                                                 Met
                                                                  1

TCG CAG CAA GAC CGA GTT GCC CCA CAG GAC CAG GAC TCG TTC CTC GAC               165
Ser Gln Gln Asp Arg Val Ala Pro Gln Asp Gln Asp Ser Phe Leu Asp
            5                   10                  15

GAC CAG CCC GGC GTC CGC CCG ATC CCG TCC TTC GAT GAC ATG CCG TTG               213
Asp Gln Pro Gly Val Arg Pro Ile Pro Ser Phe Asp Asp Met Pro Leu
        20                  25                  30

CAC CAG AAC CTT CTG CGC GGC ATC TAC TCG TAC GGC TTC GAG AAA CCG               261
His Gln Asn Leu Leu Arg Gly Ile Tyr Ser Tyr Gly Phe Glu Lys Pro
    35                  40                  45

TCC AGC ATC CAG CAG CGC GCC ATC GCC CCC TTC ACG CGC GGC GGC GAC               309
Ser Ser Ile Gln Gln Arg Ala Ile Ala Pro Phe Thr Arg Gly Gly Asp
50                  55                  60                  65

ATC ATC GCG CAG GCG CAG TCC GGT ACC GGC AAG ACG GGC GCC TTC TCC               357
Ile Ile Ala Gln Ala Gln Ser Gly Thr Gly Lys Thr Gly Ala Phe Ser
                70                  75                  80

ATC GGC CTG CTG CAG CGC CTG GAC TTC CGC CAC AAC CTG ATC CAG GGC               405
Ile Gly Leu Leu Gln Arg Leu Asp Phe Arg His Asn Leu Ile Gln Gly
            85                  90                  95

CTC GTG CTC TCC CCG ACC CGC GAG CTG GCC CTG CAG ACG GCG GAG GTG               453
Leu Val Leu Ser Pro Thr Arg Glu Leu Ala Leu Gln Thr Ala Glu Val
        100                 105                 110

ATC AGC CGC ATC GGC GAG TTC CTG TCG AAC AGC GCG AAG TTC TGT GAG               501
Ile Ser Arg Ile Gly Glu Phe Leu Ser Asn Ser Ala Lys Phe Cys Glu
    115                 120                 125

ACC TTT GTG GGT GGC ACG CGT GTG CAG GAT GAC CTG CGC AAG CTG CAG               549
Thr Phe Val Gly Gly Thr Arg Val Gln Asp Asp Leu Arg Lys Leu Gln
130                 135                 140                 145

GCT GGC GTC GTC GTC GCC GTG GGG ACG CCG GGC CGC GTG TCC GAC GTG               597
Ala Gly Val Val Val Ala Val Gly Thr Pro Gly Arg Val Ser Asp Val
                150                 155                 160

ATC AAG CGC GGC GCG CTG CGC ACC GAG TCC CTG CGC GTG CTG GTG CTC               645
Ile Lys Arg Gly Ala Leu Arg Thr Glu Ser Leu Arg Val Leu Val Leu
            165                 170                 175

GAC GAG GCT GAT GAG ATG CTG TCT CAG GGC TTC GCG GAT CAG ATT TAC               693
Asp Glu Ala Asp Glu Met Leu Ser Gln Gly Phe Ala Asp Gln Ile Tyr
        180                 185                 190

GAG ATC TTC CGC TTC CTG CCG AAG GAC ATC CAG GTC GCG CTC TTC TCC               741
Glu Ile Phe Arg Phe Leu Pro Lys Asp Ile Gln Val Ala Leu Phe Ser
    195                 200                 205
```

| GCC | ACG | ATG | CCG | GAG | GAG | GTG | CTG | GAG | CTG | ACA | AAG | AAG | TTC | ATG | CGC | 789 |
| Ala | Thr | Met | Pro | Glu | Glu | Val | Leu | Glu | Leu | Thr | Lys | Lys | Phe | Met | Arg | |
| 210 | | | | 215 | | | | | 220 | | | | | | 225 | |

| GAC | CCC | GTA | CGC | ATT | CTC | GTG | AAG | CGC | GAG | AGC | CTG | ACG | CTG | GAG | GGC | 837 |
| Asp | Pro | Val | Arg | Ile | Leu | Val | Lys | Arg | Glu | Ser | Leu | Thr | Leu | Glu | Gly | |
| | | | | 230 | | | | | 235 | | | | | 240 | | |

| ATC | AAG | CAG | TTC | TTC | ATC | GCC | GTC | GAG | GAG | GAG | CAC | AAG | CTG | GAC | ACG | 885 |
| Ile | Lys | Gln | Phe | Phe | Ile | Ala | Val | Glu | Glu | Glu | His | Lys | Leu | Asp | Thr | |
| | | | 245 | | | | | 250 | | | | | 255 | | | |

| CTG | ATG | GAC | CTG | TAC | GAG | ACC | GTG | TCC | ATC | GCG | CAG | TCC | GTC | ATC | TTC | 933 |
| Leu | Met | Asp | Leu | Tyr | Glu | Thr | Val | Ser | Ile | Ala | Gln | Ser | Val | Ile | Phe | |
| | | 260 | | | | | 265 | | | | | 270 | | | | |

| GCC | AAC | ACC | CGC | CGC | AAG | GTG | GAC | TGG | ATC | GCC | GAG | AAG | CTG | AAT | CAG | 981 |
| Ala | Asn | Thr | Arg | Arg | Lys | Val | Asp | Trp | Ile | Ala | Glu | Lys | Leu | Asn | Gln | |
| | 275 | | | | | 280 | | | | | 285 | | | | | |

| AGC | AAC | CAC | ACC | GTC | AGC | AGC | ATG | CAC | GCC | GAG | ATG | CCC | AAG | AGC | GAC | 1029 |
| Ser | Asn | His | Thr | Val | Ser | Ser | Met | His | Ala | Glu | Met | Pro | Lys | Ser | Asp | |
| 290 | | | | | 295 | | | | | 300 | | | | | 305 | |

| CGC | GAG | CGC | GTC | ATG | AAC | ACC | TTC | CGC | AGC | GGC | AGC | TCC | CGC | GTG | CTC | 1077 |
| Arg | Glu | Arg | Val | Met | Asn | Thr | Phe | Arg | Ser | Gly | Ser | Ser | Arg | Val | Leu | |
| | | | | 310 | | | | | 315 | | | | | 320 | | |

| GTA | ACG | ACC | GAC | CTC | GTG | GCC | CGC | GGC | ATC | GAC | GTG | CAC | CAC | GTG | AAC | 1125 |
| Val | Thr | Thr | Asp | Leu | Val | Ala | Arg | Gly | Ile | Asp | Val | His | His | Val | Asn | |
| | | | 325 | | | | | 330 | | | | | 335 | | | |

| ATC | GTC | ATC | AAC | TTC | GAC | CTG | CCG | ACG | AAC | AAG | GAG | AAC | TAC | CTG | CAC | 1173 |
| Ile | Val | Ile | Asn | Phe | Asp | Leu | Pro | Thr | Asn | Lys | Glu | Asn | Tyr | Leu | His | |
| | | 340 | | | | | 345 | | | | | 350 | | | | |

| CGC | ATT | GGC | CGC | GGC | GGC | CGC | TAC | GGC | GTA | AAG | GGT | GTT | GCC | ATC | AAC | 1221 |
| Arg | Ile | Gly | Arg | Gly | Gly | Arg | Tyr | Gly | Val | Lys | Gly | Val | Ala | Ile | Asn | |
| | | 355 | | | | | 360 | | | | | 365 | | | | |

| TTC | GTG | ACG | GAG | AAA | GAC | GTG | GAG | CTG | CTG | CAC | GAG | ATC | GAG | GGG | CAC | 1269 |
| Phe | Val | Thr | Glu | Lys | Asp | Val | Glu | Leu | Leu | His | Glu | Ile | Glu | Gly | His | |
| 370 | | | | 375 | | | | | 380 | | | | | | 385 | |

| TAC | CAC | ACG | CAG | ATC | GAT | GAG | CTC | CCG | GTG | GAC | TTT | GCC | GCC | TAC | CTC | 1317 |
| Tyr | His | Thr | Gln | Ile | Asp | Glu | Leu | Pro | Val | Asp | Phe | Ala | Ala | Tyr | Leu | |
| | | | | 390 | | | | | 395 | | | | | 400 | | |

| GGC | GAG | TGA | GCGGGCCCT | GCCCCCTTC | CCTGCCCCC | TCTCGCGACG | | | | | | | | | | 1366 |
| Gly | Glu | | | | | | | | | | | | | | | |

| AGAGAACGCA | CATCGTAACA | CAGCCACGCG | AACGATAGTA | AGGGCGTGCG | GCGGCGTTCC | 1426 |

| CCTCCTCCTG | CCAGCGGCCC | CCCTCCGCAG | CGCTTCTCTT | TTGAGAGGGG | GGCAGGGGGA | 1486 |

| GGCGCTGCGC | CTGGCTGGAT | GTGTGCTTGA | GCTTGCATTC | CGTCAAGCAA | GTGCTTTGTT | 1546 |

| TTAATTATGC | GCGCCGTTTT | GTTGCTCGTC | CCTTTCGTTG | GTGTTTTTTC | GGCCGAAACG | 1606 |

| GCGTTTAAAG | CA | | | | | 1618 |

( 2 ) INFORMATION FOR SEQ ID NO:2:

( i ) SEQUENCE CHARACTERISTICS:
        ( A ) LENGTH: 403 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Gln | Gln | Asp | Arg | Val | Ala | Pro | Gln | Asp | Gln | Asp | Ser | Phe | Leu |
| 1 | | | | 5 | | | | | 10 | | | | | 15 | |

| Asp | Asp | Gln | Pro | Gly | Val | Arg | Pro | Ile | Pro | Ser | Phe | Asp | Asp | Met | Pro |
| | | | 20 | | | | | 25 | | | | | 30 | | |

| Leu | His | Gln | Asn | Leu | Leu | Arg | Gly | Ile | Tyr | Ser | Tyr | Gly | Phe | Glu | Lys |

|  |  | 35 |  |  |  | 40 |  |  |  | 45 |  |  |
|---|---|---|---|---|---|---|---|---|---|---|---|---|

Pro Ser Ser Ile Gln Gln Arg Ala Ile Ala Pro Phe Thr Arg Gly Gly
          50                      55                      60

Asp Ile Ile Ala Gln Ala Gln Ser Gly Thr Gly Lys Thr Gly Ala Phe
 65              70                      75                      80

Ser Ile Gly Leu Leu Gln Arg Leu Asp Phe Arg His Asn Leu Ile Gln
              85                      90                      95

Gly Leu Val Leu Ser Pro Thr Arg Glu Leu Ala Leu Gln Thr Ala Glu
            100                     105                    110

Val Ile Ser Arg Ile Gly Glu Phe Leu Ser Asn Ser Ala Lys Phe Cys
          115                     120                    125

Glu Thr Phe Val Gly Gly Thr Arg Val Gln Asp Asp Leu Arg Lys Leu
    130                         135                140

Gln Ala Gly Val Val Val Ala Val Gly Thr Pro Gly Arg Val Ser Asp
145                         150                155                    160

Val Ile Lys Arg Gly Ala Leu Arg Thr Glu Ser Leu Arg Val Leu Val
                  165                     170                    175

Leu Asp Glu Ala Asp Glu Met Leu Ser Gln Gly Phe Ala Asp Gln Ile
                180                     185                     190

Tyr Glu Ile Phe Arg Phe Leu Pro Lys Asp Ile Gln Val Ala Leu Phe
        195                     200                    205

Ser Ala Thr Met Pro Glu Glu Val Leu Glu Leu Thr Lys Lys Phe Met
    210                     215                    220

Arg Asp Pro Val Arg Ile Leu Val Lys Arg Glu Ser Leu Thr Leu Glu
225                     230                    235                    240

Gly Ile Lys Gln Phe Phe Ile Ala Val Glu Glu His Lys Leu Asp
                  245                    250                    255

Thr Leu Met Asp Leu Tyr Glu Thr Val Ser Ile Ala Gln Ser Val Ile
            260                     265                    270

Phe Ala Asn Thr Arg Arg Lys Val Asp Trp Ile Ala Glu Lys Leu Asn
          275                     280                    285

Gln Ser Asn His Thr Val Ser Ser Met His Ala Glu Met Pro Lys Ser
    290                     295                    300

Asp Arg Glu Arg Val Met Asn Thr Phe Arg Ser Gly Ser Ser Arg Val
305                     310                    315                    320

Leu Val Thr Thr Asp Leu Val Ala Arg Gly Ile Asp Val His His Val
                325                     330                    335

Asn Ile Val Ile Asn Phe Asp Leu Pro Thr Asn Lys Glu Asn Tyr Leu
          340                     345                    350

His Arg Ile Gly Arg Gly Gly Arg Tyr Gly Val Lys Gly Val Ala Ile
        355                     360                    365

Asn Phe Val Thr Glu Lys Asp Val Glu Leu Leu His Glu Ile Glu Gly
    370                     375                    380

His Tyr His Thr Gln Ile Asp Glu Leu Pro Val Asp Phe Ala Ala Tyr
385                     390                    395                    400

Leu Gly Glu ( 2 ) INFORMATION FOR SEQ ID NO:3:

( i ) SEQUENCE CHARACTERISTICS:
        ( A ) LENGTH: 1867 base pairs
        ( B ) TYPE: nucleic acid
        ( C ) STRANDEDNESS: single
        ( D ) TOPOLOGY: linear ( i x ) FEATURE:

( A ) NAME/KEY: CDS
( B ) LOCATION: 117..1325

( x i ) SEQUENCE DESCRIPTION: SEQ ID NO:3:

```
CTTTATTGTT GATTCCGCC  TTCTGAACAG CCCTCATTTT TTTTTGGTTT ACCTCTCGTT           60

GCTTGTGACG CCCCTCCCCC TCTTCACCCA TCAAGCACCC CCTGTCGTCC TCCATC             116

ATG GCG CAG AAT GAT AAG ATC GCC CCC CAG GAC CAG GAC TCC TTC CTC           164
Met Ala Gln Asn Asp Lys Ile Ala Pro Gln Asp Gln Asp Ser Phe Leu
1               5                   10                  15

GAT GAC CAG CCC GGC GTT CGC CCG ATC CCG TCC TTC GAC GAC ATG CCG           212
Asp Asp Gln Pro Gly Val Arg Pro Ile Pro Ser Phe Asp Asp Met Pro
            20                  25                  30

CTG CAC CAG AAC CTG CTG CGT GGC ATC TAC TCG TAC GGG TTC GAG AAG           260
Leu His Gln Asn Leu Leu Arg Gly Ile Tyr Ser Tyr Gly Phe Glu Lys
        35                  40                  45

CCG TCC AGC ATC CAG CAG CGC GCG ATA GCC CCC TTC ACG CGC GGC GGC           308
Pro Ser Ser Ile Gln Gln Arg Ala Ile Ala Pro Phe Thr Arg Gly Gly
    50                  55                  60

GAC ATC ATC GCG CAG GCC CAG TCC GGT ACC GGC AAG ACG GGT GCC TTC           356
Asp Ile Ile Ala Gln Ala Gln Ser Gly Thr Gly Lys Thr Gly Ala Phe
65                  70                  75                  80

TCC ATC GGT CTG CTG CAG CGC CTG GAC TTC CGC CAC AAC CTG ATC CAG           404
Ser Ile Gly Leu Leu Gln Arg Leu Asp Phe Arg His Asn Leu Ile Gln
                85                  90                  95

GGC CTC GTG CTC TCC CCC ACT CGC GAG CTG GCC CTG CAG ACG GCG GAG           452
Gly Leu Val Leu Ser Pro Thr Arg Glu Leu Ala Leu Gln Thr Ala Glu
            100                 105                 110

GTG ATC AGC CGC ATC GGT GAG TTC CTG TCG AAC AGC TCC AAG TTC TGC           500
Val Ile Ser Arg Ile Gly Glu Phe Leu Ser Asn Ser Ser Lys Phe Cys
        115                 120                 125

GAG ACC TTT GTC GGC GGC ACG CGC GTG CAG GAT GAC CTG CGC AAG CTG           548
Glu Thr Phe Val Gly Gly Thr Arg Val Gln Asp Asp Leu Arg Lys Leu
    130                 135                 140

CAG GCC GGC GTC ATC GTT GCC GTG GGC ACG CCG GGC CGC GTG TCC GAC           596
Gln Ala Gly Val Ile Val Ala Val Gly Thr Pro Gly Arg Val Ser Asp
145                 150                 155                 160

GTG ATC AAG CGT GGC GCG CTG CGC ACA GAG TCG CTG CGC GTG CTG GTG           644
Val Ile Lys Arg Gly Ala Leu Arg Thr Glu Ser Leu Arg Val Leu Val
                165                 170                 175

CTC GAC GAG GCT GAT GAG ATG CTG TCT CAG GGC TTC GCG GAC CAG ATT           692
Leu Asp Glu Ala Asp Glu Met Leu Ser Gln Gly Phe Ala Asp Gln Ile
            180                 185                 190

TAC GAG ATC TTC CGC TTC CTG CCG AAG GAC ATC CAG GTC GCG CTC TTC           740
Tyr Glu Ile Phe Arg Phe Leu Pro Lys Asp Ile Gln Val Ala Leu Phe
        195                 200                 205

TCC GCC ACG ATG CCG GAG GAG GTA CTG GAG CTG ACG AAG AAG TTC ATG           788
Ser Ala Thr Met Pro Glu Glu Val Leu Glu Leu Thr Lys Lys Phe Met
    210                 215                 220

CGC GAC CCC GTG CGT ATT CTC GTG AAG CGC GAG AGC CTG ACG CTG GAG           836
Arg Asp Pro Val Arg Ile Leu Val Lys Arg Glu Ser Leu Thr Leu Glu
225                 230                 235                 240

GGC ATC AAG CAG TTC TTC ATC GCC GTC GAA GAG GAG CAC AAG CTG GAC           884
Gly Ile Lys Gln Phe Phe Ile Ala Val Glu Glu Glu His Lys Leu Asp
                245                 250                 255

ACG CTG ATG GAC CTG TAC GAG ACC GTG TCC ATC GCG CAG TCC GTC ATC           932
Thr Leu Met Asp Leu Tyr Glu Thr Val Ser Ile Ala Gln Ser Val Ile
            260                 265                 270

TTC GCC AAC ACG CGC CGC AAG GTG GAC TGG ATC GCC GAG AAG CTG AAC           980
Phe Ala Asn Thr Arg Arg Lys Val Asp Trp Ile Ala Glu Lys Leu Asn
        275                 280                 285
```

| | | | | | | | | | | | | | | | | |
|---|---|---|---|---|---|---|---|---|---|---|---|---|---|---|---|---|
|CAG|AGC|AAC|CAC|ACC|GTC|AGC|AGC|ATG|CAC|GCC|GAG|ATG|CCC|AAG|AGC|1028|
|Gln|Ser|Asn|His|Thr|Val|Ser|Ser|Met|His|Ala|Glu|Met|Pro|Lys|Ser| |
| |290| | | |295| | | | |300| | | | | | |
|GAC|CGC|GAG|CGC|GTC|ATG|AAC|ACC|TTC|CGC|AGC|GGC|AGC|TCC|CGC|GTG|1076|
|Asp|Arg|Glu|Arg|Val|Met|Asn|Thr|Phe|Arg|Ser|Gly|Ser|Ser|Arg|Val| |
|305| | | | |310| | | | |315| | | | |320| |
|CTC|GTC|ACG|ACC|GAC|CTC|GTG|GCG|CGC|GGT|ATC|GAT|GTG|CAC|CAC|GTG|1124|
|Leu|Val|Thr|Thr|Asp|Leu|Val|Ala|Arg|Gly|Ile|Asp|Val|His|His|Val| |
| | | | |325| | | | |330| | | | |335| | |
|AAC|ATC|GTC|ATC|AAC|TTC|GAC|CTG|CCA|ACG|AAC|AAG|GAG|AAC|TAC|CTG|1172|
|Asn|Ile|Val|Ile|Asn|Phe|Asp|Leu|Pro|Thr|Asn|Lys|Glu|Asn|Tyr|Leu| |
| | | |340| | | | |345| | | | |350| | | |
|CAT|CGC|ATT|GGT|CGC|GGC|GGC|CGC|TAC|GGC|CGT|AAG|GGT|GTT|GCC|ATC|1220|
|His|Arg|Ile|Gly|Arg|Gly|Gly|Arg|Tyr|Gly|Arg|Lys|Gly|Val|Ala|Ile| |
| | |355| | | | |360| | | | |365| | | | |
|AAC|TTC|GTG|ACG|GAG|AAG|GAC|GTG|GAG|CTA|CTG|CAC|GAG|ATC|GAG|GCG|1268|
|Asn|Phe|Val|Thr|Glu|Lys|Asp|Val|Glu|Leu|Leu|His|Glu|Ile|Glu|Ala| |
|370| | | | |375| | | | |380| | | | | | |
|CAC|TAC|CAC|ACG|CAG|ATC|GAC|GAG|CTC|CCG|GTC|GAC|TTC|GCT|GCC|TAC|1316|
|His|Tyr|His|Thr|Gln|Ile|Asp|Glu|Leu|Pro|Val|Asp|Phe|Ala|Ala|Tyr| |
|385| | | | |390| | | | |395| | | | |400| |
|CTT|GGC|GAG|TAA|GCGGGTCCTT|GCCTCCCCCC|CCCTCCTCCT|CCATCCCCAT| | | | | | | | |1368|
|Leu|Gly|Glu| | | | | | | | | | | | | | |

| | | | | |
|---|---|---|---|---|
|CCCCCACCAC|CCCACACACC|CCCCCCCCGT|TCCTCGTCGG|AAGAAGAAAG|GACGCACATC|1428|
|GCCACGCGAA|GGATGACGAG|GGCTGAGGAG|GAGCTCAGGG|AACGGACTCG|TCCCCGGTGA|1488|
|GCGGGGGGAG|GAGGAGGTGA|GGCCATCGCG|CGAGCGCACC|GCCGGAAGGT|CGACCAGGGC|1548|
|GCTCAACACC|CACCCAGCAC|CCCGGTAGTT|CCCTGCCCTC|TCGTGCGCCT|CCTCTCCCAC|1608|
|CCCGTAAATC|TCCTGACGAC|TTTGTGTGGA|CCACACACGC|GCGCTCTCGC|TCCGTATCGG|1668|
|ACGCGCCCTA|TACAACACAA|CGAACCCGCC|AACGTGCCGG|TCGNCTTGTG|GATGTGTGTC|1728|
|TGGCGTAGAA|CGTGCGTCTG|CCCCCGTCCC|ATCCCATCC|CACCTCCTCG|NGTGTGTGTG|1788|
|TGTGTGTGTG|TGTGTGTGTG|TGTGTGTGTG|AGTGTGTGTG|TTTAAAAACT|ATNATNTAGA|1848|
|ATATATATCT|ATATAGGTN| | | | |1867|

( 2 ) INFORMATION FOR SEQ ID NO:4:

( i ) SEQUENCE CHARACTERISTICS:
        ( A ) LENGTH: 403 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
|Met|Ala|Gln|Asn|Asp|Lys|Ile|Ala|Pro|Gln|Asp|Gln|Asp|Ser|Phe|Leu|
|1| | | |5| | | | |10| | | | |15| |
|Asp|Asp|Gln|Pro|Gly|Val|Arg|Pro|Ile|Pro|Ser|Phe|Asp|Asp|Met|Pro|
| | | |20| | | | |25| | | | |30| | |
|Leu|His|Gln|Asn|Leu|Leu|Arg|Gly|Ile|Tyr|Ser|Tyr|Gly|Phe|Glu|Lys|
| | |35| | | | |40| | | | |45| | | |
|Pro|Ser|Ser|Ile|Gln|Gln|Arg|Ala|Ile|Ala|Pro|Phe|Thr|Arg|Gly|Gly|
| |50| | | | |55| | | | |60| | | | |
|Asp|Ile|Ile|Ala|Gln|Ala|Gln|Ser|Gly|Thr|Gly|Lys|Thr|Gly|Ala|Phe|
|65| | | | |70| | | | |75| | | | |80|
|Ser|Ile|Gly|Leu|Leu|Gln|Arg|Leu|Asp|Phe|Arg|His|Asn|Leu|Ile|Gln|
| | | | |85| | | | |90| | | | |95| |

| | | | | | | | | | | | | |
|---|---|---|---|---|---|---|---|---|---|---|---|---|
| Gly | Leu | Val | Leu<br>100 | Ser | Pro | Thr | Arg<br>105 | Glu | Leu | Ala | Leu<br>110 | Gln | Thr | Ala | Glu |
| Val | Ile | Ser<br>115 | Arg | Ile | Gly | Glu | Phe<br>120 | Leu | Ser | Asn | Ser<br>125 | Lys | Phe | Cys |
| Glu | Thr<br>130 | Phe | Val | Gly | Gly | Thr<br>135 | Arg | Val | Gln | Asp<br>140 | Asp | Leu | Arg | Lys | Leu |
| Gln<br>145 | Ala | Gly | Val | Ile | Val<br>150 | Ala | Val | Gly | Thr | Pro<br>155 | Gly | Arg | Val | Ser | Asp<br>160 |
| Val | Ile | Lys | Arg | Gly<br>165 | Ala | Leu | Arg | Thr | Glu<br>170 | Ser | Leu | Arg | Val | Leu<br>175 | Val |
| Leu | Asp | Glu | Ala<br>180 | Asp | Glu | Met | Leu | Ser<br>185 | Gln | Gly | Phe | Ala | Asp<br>190 | Gln | Ile |
| Tyr | Glu | Ile<br>195 | Phe | Arg | Phe | Leu | Pro<br>200 | Lys | Asp | Ile | Gln | Val<br>205 | Ala | Leu | Phe |
| Ser | Ala<br>210 | Thr | Met | Pro | Glu | Glu<br>215 | Val | Leu | Glu | Leu | Thr<br>220 | Lys | Lys | Phe | Met |
| Arg<br>225 | Asp | Pro | Val | Arg | Ile<br>230 | Leu | Val | Lys | Arg | Glu<br>235 | Ser | Leu | Thr | Leu | Glu<br>240 |
| Gly | Ile | Lys | Gln | Phe<br>245 | Phe | Ile | Ala | Val | Glu<br>250 | Glu | His | Lys | Leu<br>255 | Asp |
| Thr | Leu | Met | Asp<br>260 | Leu | Tyr | Glu | Thr | Val<br>265 | Ser | Ile | Ala | Gln | Ser<br>270 | Val | Ile |
| Phe | Ala | Asn<br>275 | Thr | Arg | Arg | Lys | Val<br>280 | Asp | Trp | Ile | Ala | Glu<br>285 | Lys | Leu | Asn |
| Gln | Ser<br>290 | Asn | His | Thr | Val | Ser<br>295 | Ser | Met | His | Ala | Glu<br>300 | Met | Pro | Lys | Ser |
| Asp<br>305 | Arg | Glu | Arg | Val | Met<br>310 | Asn | Thr | Phe | Arg | Ser<br>315 | Gly | Ser | Ser | Arg | Val<br>320 |
| Leu | Val | Thr | Thr | Asp<br>325 | Leu | Val | Ala | Arg | Gly<br>330 | Ile | Asp | Val | His | His<br>335 | Val |
| Asn | Ile | Val | Ile<br>340 | Asn | Phe | Asp | Leu | Pro<br>345 | Thr | Asn | Lys | Glu | Asn<br>350 | Tyr | Leu |
| His | Arg | Ile<br>355 | Gly | Arg | Gly | Gly | Arg<br>360 | Tyr | Gly | Arg | Lys | Gly<br>365 | Val | Ala | Ile |
| Asn | Phe<br>370 | Val | Thr | Glu | Lys | Asp<br>375 | Val | Glu | Leu | Leu | His<br>380 | Glu | Ile | Glu | Ala |
| His<br>385 | Tyr | His | Thr | Gln | Ile<br>390 | Asp | Glu | Leu | Pro | Val<br>395 | Asp | Phe | Ala | Ala | Tyr<br>400 |
| Leu | Gly | Glu | | | | | | | | | | | | | |

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGACGGGGTC ACCCACACTG TGCCCATCTA 30

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTAGAAGCAT TGCGGTGGAC GATGGAGGG 29

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ATGTACAGGA TGCAACTCCT GTCTT 25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTCAGTGTTG AGATGATGCT TTGAC 25

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATGGGTCTCA CCTCCCAACT GCT 23

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGAACACTTT GAATATTTCT CTCTCAT 27

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATGAAATATA CAAGTTATAT CTTGGCTTT 29

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GATGCTCTTC  GACCTCGAAA  CAGCAT                                                                    2 6
```

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TCTCAAGGGG  CTGGGTCAGC  TATCCCA                                                                   2 7
```

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
ATGCCCCAAG  CTGAGAACCA  AGACCCA                                                                   2 7
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( x i ) SEQUENCE DESCRIPTION: SEQ ID NO:15:

```
Arg  Gly  Tyr  Val  Tyr  Gln  Gly  Leu
1                      5
```

METHODS FOR ENHANCEMENT OF PROTECTIVE IMMUNE RESPONSES

CROSS-REFERENCE TO RELATED APPLICATIONS

This application is a continuation-in-part of U.S. application Ser. No. 08/607,509 filed Feb. 23, 1996, which is a continuation-in-part of U.S. application Ser. No. 08/488,386, filed Jun. 6, 1995, now abandoned, which is a continuation-in-part of U.S. application Ser. No. 08/232,534, filed Apr. 22, 1994, now abandoned.

TECHNICAL FIELD

The present invention relates generally to compounds and methods for enhancing immune responses in patients, as well as in isolated cells and cell cultures. The invention is more particularly related to compounds comprising all or a portion of a Leishmania antigen that is a homologue of the eukaryotic initiation factor 4A (eIF4A), and to the use of such compounds in vaccines for stimulating immune responses.

BACKGROUND OF THE INVENTION

Vaccines commonly induce immunity to an infection or a disease by generating an immune response in a patient to a specific antigen associated with the infection or disease. Modem techniques for the identification and use of appropriate antigens have the potential to lead to the testing and development of a large number of vaccines specific for common infections (including bacterial, viral and protozoan infections), as well as diseases such as cancer.

However, in many cases, purified antigens are weak immunogens, i.e., the immune response generated by a specific antigen, while directed against the desired target, is not of a sufficient magnitude to confer immunity. In such cases, an immunomodulating agent, such as an adjuvant or immunostimulant, must be employed to enhance the immune response. Adjuvants are substances that enhance a specific immune response to an antigen when injected with the antigen or at the same site as the antigen. Such substances function by a variety of mechanisms, including (1) trapping the antigen, and releasing it slowly, (2) stimulating migration of cells to the injection site, (3) stimulating or trapping lymphocytes, or stimulating lymphocyte proliferation and (4) improving antigen dispersion within the patient's body. For example, oils, polymers, mineral salts and liposomes have been used as adjuvants in this regard. By comparison, immunostimulants are substances that induce a general, temporary increase in a patient's immune response, whether administered with the antigen or separately. Typical immunostimulants are bacterial, such as BCG (an attenuated strain of *Mycobacterium tuberculosis*) or a nonviable form of *Corynebacterium parvum*. By either mechanism, the adjuvant or immunostimulant serves to enhance the desired specific immune response by non-specific means.

A serious drawback of many of the adjuvants currently available is their toxicity. In general, the best adjuvants (i.e., those that provide the greatest enhancement of the desired immune response) are also the most toxic. Thus, practitioners must continually balance the level of stimulation against the toxicity of the adjuvant.

Accordingly, there is a need in the art for the identification of compounds that provide a desired enhancement of specific immune responses, but with low levels of toxicity. The present invention fulfills these needs and further provides other related advantages.

SUMMARY OF THE INVENTION

Briefly stated, the present invention provides compounds and methods relating to the Leishmania antigen LbeIF4A or LmeIF4A, which is homologous to the eukaryotic ribosomal protein eIF4A. In one aspect of the invention, methods are provided for enhancing or eliciting an immune response to an antigen and/or an antigen encoded by a DNA vaccine in a patient, comprising administering to a patient an antigen and/or a DNA vaccine, and an LbeIF4A polypeptide comprising an amino acid sequence encoded by a DNA sequence selected from the group consisting of: (a) nucleotides 115–1323 of SEQ ID NO. 1; and (b) DNA sequences that hybridize to a nucleotide sequence complementary to nucleotides 115–1323 of SEQ ID NO. 1 under moderately stringent conditions, wherein the DNA sequence encodes a polypeptide that stimulates a Th1 immune response in a peripheral blood mononuclear cells obtained from a Leishmania-infected individual. In another aspect of the invention, methods are provided for enhancing or eliciting an immune response to an antigen and/or an antigen encoded by a DNA vaccine, in a patient, comprising administering to a patient an antigen and/or a DNA vaccine, and an LmeIF4A polypeptide comprising an amino acid sequence encoded by a DNA sequence selected from the group consisting of: (a) nucleotides 117 through 1325 of SEQ ID NO:3; and (b) DNA sequences that hybridize to a nucleotide sequence complementary to nucleotides 117 through 1325 of SEQ ID NO:3 under moderately stringent conditions, wherein the DNA sequence encodes a polypeptide that stimulates a Th1 immune response in peripheral blood mononuclear cells obtained from a Leishmania-infected individual.

In related aspects, the present invention provides methods for enhancing an immune response to an antigen and/or an antigen encoded by a DNA vaccine in a patient, comprising administering to a patient an antigen and/or a DNA vaccine, and an LbeIF4A polypeptide comprising amino acids 49–403 of SEQ ID NO: 2, or a variant thereof that differs only in conservative substitutions and/or modifications, or an antigen and/or a DNA vaccine and an LmeIF4A polypeptide comprising amino acids 49–403 of SEQ ID NO: 4, or a variant thereof that differs only in conservative substitutions and/or modifications.

In another related aspect, methods are provided for enhancing an immune response in a biological sample, comprising contacting a biological sample with an antigen and/or an antigen encoded by a DNA vaccine, and an LbeIF4A polypeptide as described above, wherein the biological sample comprises cells selected from the group consisting of peripheral blood mononuclear cells, monocytes, B cells, dendritic cells, and combinations thereof In yet another related aspect, methods are provided for enhancing or eliciting an immune response in a biological sample, comprising contacting a biological sample with an LmeIF4A polypeptide as described above, wherein the biological sample comprises cells selected from the group consisting of peripheral blood mononuclear cells, monocytes, B cells, dendritic cells and combinations thereof.

In another aspect, methods are provided for enhancing an immune response to a tumor in a patient, comprising administering to a patient a tumor antigen or antigens and/or a DNA vaccine, and an LbeIF4A or an LmeIF4A polypeptide as described above.

In yet another aspect, methods are provided for treating a tumor in a patient, comprising administering to a patient an LbeIF4A or LmeIF4A polypeptide, as described above.

Within each of the aspects noted above, as an alternative to utilizing an LbeIF4A or LmeIF4A polypeptide, one can utilize viral vectors or nucleic acid molecules (collectively, the "nucleic acid compositions") directing the expression of the polypeptide in patient cells infected or transfected with the nucleic acid compositions. The step of administering the nucleic acid composition may be performed in vivo or ex vivo, the latter including the subsequent administration of the infected/transfected cells. In addition, where an antigen or tumor antigen is administered, it will be evident that the nucleic acid composition may also be designed to direct the expression of such antigens (either on the same or different vectors or molecules).

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 21 shows tumor regression following administration of soluble LmeIF4A polypeptide and tumor antigen contained in microspheres.

DETAILED DESCRIPTION OF THE INVENTION

Figures 1A, 1B:
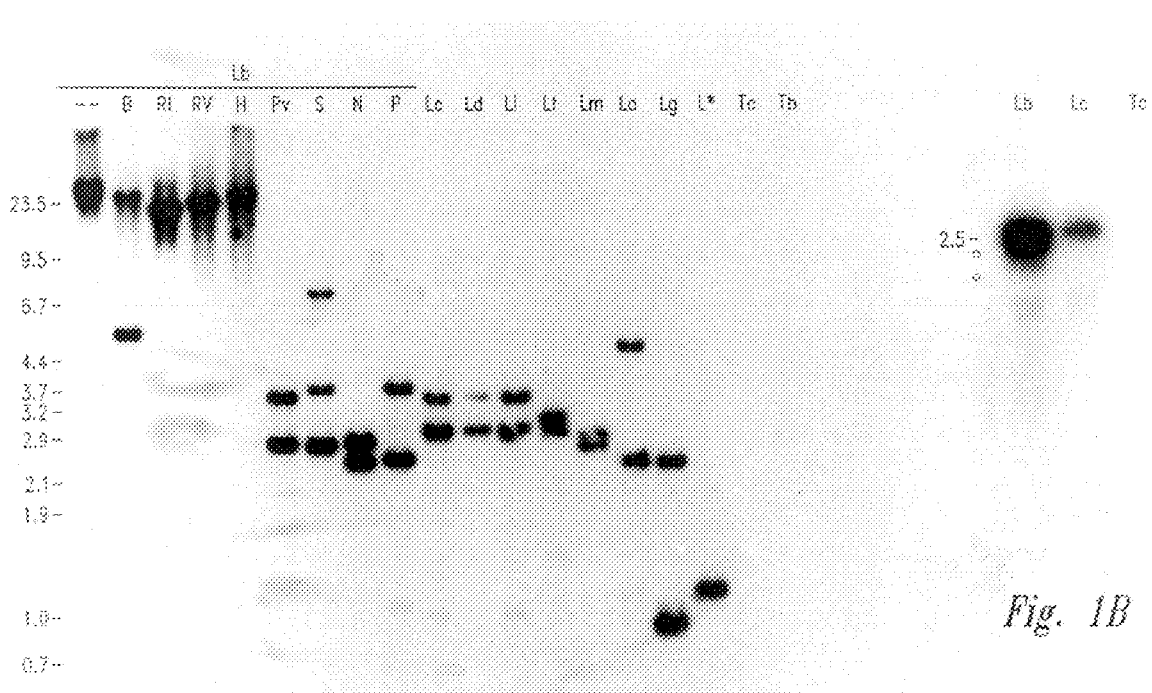
FIG. 1 presents the results of Southern blot analysis of Leishmania spp. DNA, indicating that the Leishmania eIF4A homologue is conserved and that *L. braziliensis* genomic DNA contains at least two copies of LbeIF4A.

As noted above, the present invention is generally directed to the enhancement of immune responses, which may be humoral and/or cell-mediated, in a patient or cell culture. Within the context of this invention, an immune response to an antigen, including an immunostimulating antigen (i.e., an antigen against which a patient raises an immune response), may be initiated or enhanced by administering to the patient the antigen and one or more LbeIF4A-derived or LmeIF4A-derived polypeptides as described herein. Antigens and immunostimulating antigens are in general protein molecules and include molecules derived from viruses, such as HIV, HBV, influenza virus, respiratory syncytial virus, bacteria, such as *Hemophilus influenza*, *Pneumoccocus pneumoniae*, and parasites, such as Leishmania, and Trypanosoma. In addition, an immune response to a tumor may be enhanced or elicited by administering to the patient a tumor antigen (i.e., an antigen that stimulates an immune response (e.g., CTL) to a tumor). Within the context of this invention, tumor antigens include virally encoded molecules, MAGE-1, Her-2, PSA, and other molecules. Accordingly, the methods of this invention involve the co-administration of a specific antigen or immunostimulating antigen and an LeIF4A-derived polypeptide as disclosed herein. A tumor may also be treated by administering to the patient an LbeIF4A or LmeIF4A polypeptide in the absence of such an exogenously administered tumor antigen.

The LbeIF4A and LmeIF4A polypeptides of the present invention may also be used to elicit or enhance an immune response to an antigen encoded by a DNA vaccine. DNA vaccines encode one or more immunostimulating antigens, such that the antigen is generated in situ. For instance, the DNA vaccine may encode a tumor antigen and, optionally, an LeIF4A-derived polypeptide as described herein. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. The DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells. The compounds of this invention generally comprise a polypeptide that stimulates a Th1 or CTL (cytotoxic T lymphocyte) immune response in peripheral blood mononuclear cells (PBMCs). In particular, polypeptides comprising all or a stimulatory portion of a *Leishmania braziliensis* or *Leishmania major* homologue of the eukaryotic ribosomal protein eIF4A (referred to herein as LbeIF4A and LmeIF4A) are disclosed. As used herein, the term "PBMCs" refers to preparations of nuclear cells that are present in peripheral blood. The term "polypeptide," in the context of this invention, encompasses amino acid chains of any length, including full length proteins and portions thereof, wherein amino acid residues are linked by covalent peptide bonds. Therefore, an "LbeIF4A polypeptide" comprises LbeIF4A, or a portion or other variant thereof that retains stimulatory activity. Similarly, an "LmeIF4A polypeptide" comprises LmeIF4A, or a portion or other variant thereof that retains stimulatory activity. As used herein, "LeIF4A" refers to either LbeIF4A or LmeIF4A. Although LbeIF4A is described herein for exemplary purposes, within the context of this invention, LmeIF4A, portions thereof, and variants of the polypeptide (or portions thereof) may also be used. An LeIF4A polypeptide may consist entirely of one or more stimulatory portions of LeIF4A, or the stimulatory portion (s) may be supplied in the context of a larger protein that contains additional LeIF4A sequences and/or amino acid sequences heterologous to LeIF4A. Preferably, the polypeptides are substantially free of contaminating endogenous materials.

The polypeptides of the present invention include variants of LbeIF4A that retain the ability to stimulate a Th1 or CTL immune response in PBMCs. Such variants include various structural forms of the primary protein. Due to the presence of ionizable amino and carboxyl groups, for example, a LbeIF4A polypeptide may be in the form of an acidic or basic salt, or may be in neutral form. Individual amino acid residues may also be modified by oxidation or reduction.

Variants within the scope of this invention also include polypeptides in which the primary amino acid structure of LbeIF4A or a fragment thereof is modified by forming covalent or aggregative conjugates with other polypeptides or chemical moieties such as glycosyl groups, lipids, phosphate, acetyl groups and the like. Covalent derivatives may be prepared, for example, by linking particular functional groups to amino acid side chains or at the N- or C-termini. Alternatively, for derivatives in which a polypeptide is joined to a LbeIF4A polypeptide, a fusion protein may be prepared using recombinant DNA techniques, as described below. In one such embodiment, the LbeIF4A polypeptide may be conjugated to a signal (or leader) polypeptide sequence at the N-terminal region of the protein which co-translationally or post-translationally directs transfer of the protein from its site of synthesis to its site of function inside or outside of the cell membrane or wall (e.g., the yeast $\alpha$-factor leader).

Protein fusions within the present invention may also comprise peptides added to facilitate purification or identification of LbeIF4A polypeptides (e.g., poly-His). For example, the peptide described by Hopp et al., *Bio/Technology* 6:1204 (1988) is a highly antigenic peptide that can be used to facilitate identification. Such a peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E coli.*

Protein fusions encompassed by this invention further include, for example, LeIF4A polypeptides linked to an immunoglobulin Fc region. If LbeIF4A fusion proteins are made with both heavy and light chains of an antibody, it is possible to form a protein oligomer with as many as four LbeIF4A protein regions. Also within the scope of the present invention are LbeIF4A polypeptides linked to a leucine zipper domain. Leucine zipper domains are described, for example, in published PCT Application WO 94/10308. LbeIF4A polypeptides comprising leucine zippers may, for example, be oligomeric, dimeric or trimeric. All of the above protein fusions may be prepared by chemical linkage or as fusion proteins, as described below.

Preferred protein fusions include polypeptides that comprise sequences useful for stimulating immunity to infectious pathogens (e.g., antigens). Such sequences may be derived, for example, from viruses, tumor cells, parasites or bacteria.

The present invention also includes LeIF4A polypeptides with or without associated native-pattern glycosylation. Polypeptides expressed in yeast or mammalian expression systems may be similar to or slightly different in molecular weight and glycosylation pattern than the native molecules, depending upon the expression system. For instance, expression of DNA encoding LbeIF4A polypeptides in bacteria such as *E. coli* provides non-glycosylated molecules. N-glycosylation sites of eukaryotic proteins are characterized by the amino acid triplet Asn-$A_1$-Z, where $A_1$ is any amino acid except Pro, and Z is Ser or Thr. Variants of LbeIF4A polypeptides having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a LbeIF4A polypeptide.

The polypeptides of this invention also include variants of LeIF4A polypeptides that have an amino acid sequence different from the native LeIF4A protein because of one or more deletions, insertions, substitutions or other modifications. Such variants should be substantially homologous to the native LeIF4A and should retain the ability to stimulate a Th1 or CTL immune response in PBMCs. "Substantial homology," as used herein, refers to amino acid sequences that may be encoded by DNA sequences that are capable of hybridizing under moderately stringent conditions to a naturally occurring DNA sequence encoding, for instance, LbeIF4A. Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS). Such hybridizing DNA sequences are also within the scope of this invention. The effect of any such modifications on the activity of a LbeIF4A polypeptide may be readily determined by analyzing the ability of the mutated LbeIF4A peptide to induce a Th1 or CTL response using, for example, any of the methods described herein. A preferred variant of LbeIF4A is the *Leishmania major* homologue of LbeIF4A (LmeIF4A).

Generally, amino acid substitutions should be made conservatively; i.e., a substitute amino acid should replace an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants within the scope of this invention may also, or alternatively, contain other modifications, including the deletion or addition of amino acids, that have minimal influence on the stimulatory properties, secondary structure and hydropathic nature of the polypeptide. In general, fragments of LbeIF4A may be constructed by deleting terminal or internal residues or sequences. Additional guidance as to suitable modifications may be obtained by a comparison of the sequence of LbeIF4A to the sequences and structures of other eIF4A family members. For example, terminal or internal residues or sequences of LbeIF4A not needed for biological activity may be deleted. Cysteine residues may be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

An LeIF4A full length protein may generally be obtained using a genomic or cDNA clone encoding the protein. A genomic sequence that encodes full length LbeIF4A is shown in SEQ ID NO:1, and the deduced amino acid sequence is presented in SEQ ID NO:2. A genomic sequence that encodes full length LmeIF4A is shown in SEQ ID NO:3 and the deduced amino acid sequence in SEQ ID NO:4. Such clones may be isolated by screening an appropriate *Leishmania braziliensis* or *Leishmania major* expression library for clones that express antigens that react with sera from a patient afflicted with mucosal leishmaniasis, and then analyzing the reactive antigens for the ability to stimulate proliferative responses and preferential Th1 cytokine production in patient T cell assays or for the ability to stimulate a CTL response in patient T cells. The library preparation and screen may generally be performed using methods known to those of ordinary skill in the art, such as methods described in Sambrook et al., *Molecular Cloning: A Laboratory Manual*, Cold Spring Harbor Laboratories, Cold Spring Harbor, N.Y., 1989, which is incorporated herein by reference. Briefly, a bacteriophage expression library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing genomic or cDNA sequences that express a protein which binds to an antibody in the serum are isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

Patient T cell assays may generally be performed by treating patient PBMCs with the reactive antigens and analyzing the cells for a suitable response. For example, the PBMC supernatant may be assayed for the level of secreted cytokines. Preferably, the cytokine assayed is interferon-γ, interleukin-2, interleukin-12 (either the p40 subunit or biologically active p70), interleukin-1 or tumor necrosis factor-α. The cytokines interleukin-4 and interleukin-10 may also be assayed, since the levels of these representative Th2-type cytokines generally decrease in response to treatment with a polypeptide as described herein. Cytokines may be assayed, for example, using commercially available antibodies specific for the cytokine of interest in an ELISA format, with positive results determined according to the manufacturer's instructions. Suitable antibodies may be obtained, for example, from Chemicon, Temucula, Calif. and PharMingen, San Diego, Calif. Alternatively, the treated PBMCs may be assayed for mRNA encoding one or more of the cytokines interferon-γ, interleukin-2, interleukin-12 p40 subunit, interleukin-1 or tumor necrosis factor-α, or the PBMCs may be assayed for a proliferative response as described herein. Alternatively, cytokines may be measured by testing PBMC supernatants for cytokine-specific biological activities.

Variants of LbeIF4A that retain the ability to stimulate a Th1 immune response in PBMCs may generally be identified by modifying the sequence in one or more of the aspects described above and assaying the resulting polypeptide for the ability to stimulate a Th1 response. Such assays may generally be performed by treating patient PBMCs with the modified polypeptide and assaying the response, as described above. Naturally occurring variants of LbeIF4A may also be isolated from other Leishmania species by, for example, screening an appropriate cDNA or genomic library with a DNA sequence encoding LbeIF4A or a variant thereof.

The above-described sequence modifications may be introduced using standard recombinant techniques or by automated synthesis of the modified polypeptide. For example, mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed site-specific mutagenesis procedures can be employed to provide a gene in which particular codons are altered according to the substitution, deletion, or insertion required. Exemplary methods of making the alterations set forth above are disclosed by Walder et al., *Gene* 42:133, 1986; Bauer et al.,

*Gene* 37:73, 1985; Craik, *BioTechniques*, Jan. 1985, 12–19; Smith et al., *Genetic Engineering: Principles and Methods*, Plenum Press, 1981; and U.S. Pat. Nos. 4,518,584 and 4,737,462.

Mutations in nucleotide sequences constructed for expression of such LbeIF4A polypeptides must, of course, preserve the reading frame of the coding sequences and preferably will not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed LbeIF4A protein mutants screened for the desired activity.

Not all mutations in a nucleotide sequence which encodes a LbeIF4A protein will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known *E. coli* preference codons for *E. coli* expression.

The polypeptides of the present invention, both naturally occurring and modified, are preferably produced by recombinant DNA methods. Such methods include inserting a DNA sequence encoding a LbeIF4A polypeptide into a recombinant expression vector and expressing the DNA sequence in a recombinant microbial, mammalian or insect cell expression system under conditions promoting expression. DNA sequences encoding the polypeptides provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors contain a DNA sequence encoding a LeIF4A polypeptide operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. An origin of replication and a selectable marker to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, in reading frame. DNA sequences encoding LeIF4A polypeptides which are to be expressed in a microorganism will preferably contain no introns that could prematurely terminate transcription of DNA into mRNA.

Expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and European Patent Application 36,776) and the tac promoter (Maniatis, *Molecular Cloning: A Laboratory Manual*, Cold Spring Harbor Laboratory, p.412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed (see, e.g., Kurjan et al., *Cell* 30:933, 1982; and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes. The transcriptional and translational control sequences in expression vectors to be used in transforming vertebrate cells may be provided by viral sources. For example, commonly used promoters and enhancers are derived from polyoma, adenovirus 2, simian virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the Bgl II site located in the viral origin of replication is included. Further, viral genomic promoter, control and/or signal sequences may be utilized, provided such control sequences are compatible with the host cell chosen. Exemplary vectors can be constructed as disclosed by Okayama and Berg, *Mol. Cell. Biol.* 3:280, 1983.

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of LbeIF4A protein DNA is pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-L/EBNA cell line was derived by transfection of the CV-1 cell line with a gene encoding Epstein-Barr virus nuclear antigen-I (EBNA-1) and constitutively express EBNA-1 driven from human CMV immediate-early enhancer/promoter.

Transformed host cells are cells which have been transformed or transfected with expression vectors constructed using recombinant DNA techniques and which contain sequences encoding a LbeIF4A polypeptide of the present invention. Transformed host cells may express the desired LbeIF4A polypeptide, but host cells transformed for purposes of cloning or amplifying LbeIF4A DNA do not need to express the LbeIF4A protein. Expressed LbeIF4A proteins will preferably be secreted into the culture supernatant, depending on the DNA selected, but may also be deposited in the cell membrane.

Suitable host cells for expression of recombinant proteins include prokaryotes, yeast or higher eukaryotic cells under the control of appropriate promoters. Prokaryotes include gram negative or gram positive organisms, for example *E. coli* or Bacilli. Higher eukaryotic cells include established cell lines of insect or mammalian origin as described below. Cell-free translation systems could also be employed to produce LbeIF4A proteins using RNAs derived from the DNA constructs disclosed herein. Appropriate cloning and expression vectors for use with bacterial, fungal, yeast, and mammalian cellular hosts are described, for example, by Pouwels et al., *Cloning Vectors: A Laboratory Manual*, Elsevier, New York, 1985.

Prokaryotic expression hosts may be used for expression of LeIF4A polypeptides that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although other hosts may also be employed.

Recombinant LbeIF4A polypeptides may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the $2\mu$ yeast plasmid or an autonomously replicating sequence (ARS), a promoter, DNA encoding the LbeIF4A polypeptide, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art. An exemplary technique described by Hind et al. (*Proc. Natl. Acad. Sci. USA* 75:1929, 1978), involves selecting for Trp$^+$ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., Spodoptera or Trichoplusia) cell culture systems can also be employed to express recombinant protein. Baculovirus systems for production of heterologous proteins in insect cells are reviewed, for example, by Luckow and Summers, *Bio/Technology* 6:47, 1988. Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purified LeIF4A polypeptides may be prepared by culturing suitable host/vector systems to express the recombinant translation products of the DNAs of the present invention, which are then purified from culture media or cell extracts. For example, supernatants from systems which secrete recombinant protein into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which LeIF4A binds in a specific interaction based on structure) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying LeIF4A.

Affinity chromatography is a particularly preferred method of purifying LbeIF4A polypeptides. For example, a LbeIF4A polypeptide expressed as a fusion protein comprising an immunoglobulin Fc region can be purified using Protein A or Protein G affinity chromatography. Moreover, a LbeIF4A protein comprising a leucine zipper domain may be purified on a resin comprising an antibody specific to the leucine zipper domain. Monoclonal antibodies against the LbeIF4A protein may also be useful in affinity chromatography purification, by utilizing methods that are well-known in the art.

Finally, one or more reverse-phase high performance liquid chromatography (RP-HPLC) steps employing hydrophobic RP-HPLC media (e.g., silica gel having pendant methyl or other aliphatic groups) can be employed to further purify a LbeIF4A protein composition. Some or all of the foregoing purification steps, in various combinations, can also be employed to provide a homogeneous recombinant protein.

Recombinant LbeIF4A polypeptide produced in bacterial culture is preferably isolated by initial extraction from cell pellets, followed by one or more concentration, salting-out, aqueous ion exchange or size exclusion chromatography steps. High performance liquid chromatography (HPLC) may be employed for final purification steps. Microbial cells employed in expression of recombinant LbeIF4A protein can be disrupted by any convenient method, including freeze-thaw cycling, sonication, mechanical disruption, or use of cell lysing agents.

Fermentation of yeast which express LbeIF4A polypeptide as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reverse-phase HPLC steps for purification of recombinant human GM-CSF on a preparative HPLC column.

Preparations of LbeIF4A polypeptides synthesized in recombinant culture may contain non-LbeIF4A cell components, including proteins, in amounts and of a character which depend upon the purification steps taken to recover the LbeIF4A protein from the culture. These components ordinarily will be of yeast, prokaryotic or non-human eukaryotic origin. Such preparations are typically free of other proteins which may be normally associated with the LbeIF4A protein as it is found in nature in its species of origin.

Automated synthesis provides an alternate method for preparing polypeptides of this invention having fewer than about 100 amino acids, and typically fewer than about 50 amino acids. For example, any of the commercially available solid-phase techniques may be employed, such as the Merrifield solid phase synthesis method, in which amino acids are sequentially added to a growing amino acid chain. (See Merrifield, *J. Am. Chem. Soc.* 85:2149–2146, 1963.) Equipment for automated synthesis of polypeptides is commercially available from suppliers such as Applied Biosystems, Inc. of Foster City, Calif., and may generally be operated according to the manufacturer's instructions.

As an alternative to the presentation of LeIF4A polypeptides, the subject invention includes compositions capable of delivering nucleic acid molecules encoding an LeIF4A polypeptide or portion thereof. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616–627, 1988; Li et al., *Hum. Gene Ther.* 4:403–409, 1993; Vincent et al., *Nat. Genet.* 5:130–134, 1993; and Kolls et al., *Proc. Natl. Acad. Sci. USA* 91:215–219, 1994), pox virus (see U.S. Pat. No. 4,769,330; U.S. Pat. No. 5,017,487; and WO 89/01973)), naked DNA (see WO 90/11092), nucleic acid molecule complexed to a polycationic molecule (see WO 93/03709), and nucleic acid associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147–154, 1992; Cotton et al., *Proc. Natl. Acad. Sci. USA* 89:6094, 1992). Other suitable compositions include DNA-ligand (see Wu et al., *J. Biol. Chem.* 264:16985–16987, 1989) and lipid-DNA combinations (see Felgner et al., *Proc. Natl. Acad. Sci. USA* 84:7413–7417, 1989). In addition, the efficiency of naked DNA uptake into cells may be increased by coating the DNA onto biodegradable latex beads.

In addition to direct in vivo procedures, ex vivo procedures may be used in which cells are removed from an animal, modified, and placed into the same or another animal. It will be evident that one can utilize any of the compositions noted above for introduction of LeIF4A nucleic acid molecules into tissue cells in an ex vivo context. Protocols for viral, physical and chemical methods of uptake are well known in the art.

As noted above, the subject invention provides methods of using the polypeptides or related nucleic acid compositions disclosed herein for enhancing or eliciting immune responses. It has been found within the present invention that LbeIF4A contains epitope(s) that stimulate proliferation of PBMCs from Leishmania-infected individuals. LbeIF4A also stimulates PBMCs from infected individuals to generate an exclusive Th1 cytokine profile. A Th1 response is characterized by the production of the cytokines interleukin-1 (IL-1), interleukin-2 (IL-2), interleukin-12 (IL-12) or interferon-$\gamma$ (IFN-$\gamma$), as well as tumor necrosis factor-$\alpha$ (TNF-$\alpha$). IL-12 is a heterodimeric molecule comprising p40 and p35 subunits, which must be coexpressed for the production of biologically active IL-12 p70. The p40 subunit is produced only by IL-12-producing cells and is induced in vitro and in vivo after bacterial and parasite stimulation, whereas the p35 subunit is both ubiquitous and constitutively expressed. Therefore, cells producing IL-12 also have a large excess (10–100 fold) of biologically inactive free p40 chains. The stimulation of IL-12 production is particularly significant as this cytokine has the ability to influence T cells towards a Th1 response (IFN-$\gamma$ and IL-2 production). The ability of a protein to stimulate IL-12 production is therefore an important adjuvant property.

LbeIF4A also stimulates a Th1 profile of mRNAs encoding IFN-$\gamma$, IL-2, IL-12 p40 subunit, and TNF-$\alpha$, in PBMCs from Leishmania infected patients. No detectable IL-4 or IL-10 mRNA, indicative of a Th2 response, is present in such stimulated PBMCs. In fact, LbeIF4A generally downregulates the expression of IL-10 mRNA present in fresh PBMCs of some leishmaniasis patients as well as the LPS-induced IL-10 production by patient and normal PBMCs. These properties of LbeIF4A suggest a role for LbeIF4A in generating a protective or therapeutic immune response in leishmaniasis patients.

In addition, LbeIF4A stimulates the production of IL-12 and IL-2 in PBMCs obtained from uninfected control individuals, as well as in cultured human macrophages, in the human myeloid leukemia cell line THP-1 and in mice. LbeIF4A also synergizes with IFN-γ to stimulate THP-1 cells to secrete IL-12, and the induction of IFN-γ production by patient PBMCs is abrogated by the presence of anti-IL-12 antibody. The ability to stimulate IL-12 and IL-2 production indicates that LbeIF4A has the ability to induce an immune response, and that the polypeptides described herein have a wide applicability in the non-specific enhancement of immune responses.

Accordingly, the present invention discloses methods for enhancing or eliciting, in a patient or cell culture, a cellular immune response (e.g., the generation of antigen-specific cytolytic T cells). The present invention also discloses methods for enhancing or eliciting a humoral immune response to an antigen (e.g., antigen-reactive antibody production) using a LbeIF4A or LmeIF4A polypeptide as described above. As used herein, the term "patient" refers to any warm-blooded animal, preferably a human. A patient may be afflicted with a disease, such as leishmaniasis (or other infectious diseases) or cancer, such as melanoma, breast cancer, prostate cancer, lymphoma, colon cancer or other tumor, or may be normal (i.e., free of detectable disease and infection). A "cell culture" is any preparation of PBMCs or isolated component cells (including, but not limited to, macrophages, monocytes, B cells and dendritic cells). Such cells may be isolated by any of a variety of techniques well known to those of ordinary skill in the art (such as Ficoll-hypaque density centrifugation). The cells may (but need not) have been isolated from a patient afflicted with leishmaniasis, or another disorder, and may be reintroduced into a patient after treatment.

Within these methods, the LeIF4A polypeptide (or nucleic acid composition) is administered to a patient or cell culture along with an antigen, such that it functions as an immunomodulating agent to enhance or elicit the immune response to the antigen. The LeIF4A polypeptide may be administered within the same preparation (e.g., vaccine) as the antigen, or may be administered separately. In one embodiment, the antigen and the LeIF4A polypeptide are administered to a patient at the same time and site. In this manner, LeIF4A polypeptides may be used, for example, as adjuvants in vaccine preparations for heterologous agents. In another embodiment, the antigen and LeIF4A polypeptide are administered at different sites on the patient. For example, the LeIF4A polypeptide could be administered (e.g., injected) in one arm, and the antigen administered in the other arm. Such administrations may, but need not, take place at the same time. Alternatively, the LeIF4A polypeptide may be administered before or after the antigen. For example, the LeIF4A polypeptide could be administered 24 hours prior to antigen administration. Suitable doses and methods of administration are presented in detail below.

The immune response generated by a patient to whom a LeIF4A polypeptide is administered may vary, depending on the condition of the patient. For Leishmania-infected patients, the immune responses that may be generated include a preferential Th1 immune response (which includes stimulation of IL-12 production) and the down-regulation of IL-10 expression. For uninfected individuals, the immune response may be the production of IL-12, the production of IL-2, the stimulation of gamma T cells, the production of interferon, the generation of antigen-reactive CTL, the production of antigen-specific antibodies or any combination thereof. Either type of response provides enhancement of the patient's immune response to the antigen administered with the LeIF4A polypeptide. In addition, for patients with diagnosed cancer, such as melanoma, breast cancer, lymphoma, colon cancer, prostate cancer and the like, the immune response may include a preferential CTL response. For treatment of a tumor, the immune response should result in a reduction in tumor mass.

The LeIF4A polypeptide (or nucleic acid composition) is preferably formulated for use in the above methods as a pharmaceutical composition or a vaccine. Pharmaceutical compositions generally comprise one or more LbeIF4A polypeptides in combination with a physiologically acceptable carrier, excipient or diluent. Such carriers will be nontoxic to recipients at the dosages and concentrations employed. The vaccines comprise one or more LbeIF4A polypeptides and one or more additional antigens appropriate for the indication. The use of LbeIF4A proteins in conjunction with soluble cytokine receptors, cytokines, and chemotherapeutic agents is also contemplated.

Routes and frequency of administration and polypeptide (or nucleic acid composition) doses will vary from individual to individual and may parallel those currently being used in immunization or treatment of other infections. In general, the pharmaceutical compositions and vaccines may be administered by injection (e.g., intramuscular, intravenous or subcutaneous), intranasally (e.g., by aspiration) or orally. The amount and frequency of administration will depend, of course, on such factors as the nature and severity of the indication being treated, the desired response, the condition of the patient, and so forth. Typically, between 1 and 4 doses may be administered for a 2–6 week period. Preferably, two doses are administered, with the second dose 2–4 weeks later than the first. A suitable dose is an amount of LbeIF4A polypeptide that stimulates the production of IL-12 in the patient, such that the amount of IL-12 in supernatants of PBMCs isolated from the patient is between about 10 ng and 10 μg per mL. In general, the amount of IL-12 may be determined using any appropriate assay known to those of ordinary skill in the art, including the assays described herein. The amount of LbeIF4A polypeptide present in a dose typically ranges from about 1 pg to about 100 mg per kg of host, typically from about 10 pg to about 1 mg, and preferably from about 100 pg to about 1 μg. Suitable dose sizes will vary with the size of the animal, but will typically range from about 0.01 mL to about 5 mL for 10–60 kg animal. Specific appropriate dosages for a particular indication can be readily determined.

Alternatively, cells, preferably peripheral blood mononuclear cells, are removed from a patient and stimulated in vitro with one of the LeIF4A polypeptides and an antigen (including a tumor antigen). Upon generation of an antigen-specific immune response, such as a CTL response, the cells may be expanded and reinfused into the patient.

While any suitable carrier known to those of ordinary skill in the art may be employed in the pharmaceutical compositions of this invention, the type of carrier will vary depending on the mode of administration and whether a sustained release administration is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109 and in U.S. patent application Ser. Nos. 08/116,484 and 08/116,802 (incorporated by reference herein). The polypeptide or polypeptide/antigen combination may be encapsulated within the biodegradable microsphere or associated with the surface of the microsphere. In this regard, it is preferable that the microsphere be larger than approximately 25 microns.

Pharmaceutical compositions and vaccines may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Optionally, any of a variety of additional agents may be employed in the vaccines or pharmaceutical compositions of this invention, in addition to the LbeIF4A polypeptide, to further nonspecifically enhance the immune response. Such agents usually contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Such agents are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The following examples are offered by way of illustration, and not by way of limitation. Those skilled in the art will recognize that variations of the invention embodied in the examples can be made, especially in light of the teachings of the various references cited herein.

EXAMPLES

Example 1

Preparation of DNA Encoding LbeIF4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(-) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T cell assays for their ability to stimulate a proliferative response, as described in Example 5, below, and a dominant Th1 cytokine profile, as described in Example 7, below.

A recombinant clone was identified in the above assays which, following sequence comparison of its predicted amino acid sequence with sequences of other proteins, was identified as a *Leishmania braziliensis* homologue of the eukaryotic initiation factor 4A (eIF4A). The isolated clone (pLeIF.1) lacked the first 48 amino acid residues (144 nucleotides) of the full length protein sequence. The pLeIF.1 insert was subsequently used to isolate the full length genomic sequence.

SEQ ID NO:1 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 2

Characterization of the LbeIF4A Gene

This example describes a Southern blot analysis of LbeIF4A DNA in Leishmania species. *Leishmania braziliensis* (MHOM/BR/75/M2903), *L. guyanensis* (MHOM/BR/75/M4147) *L. amazonensis* (IFLA/BR/67/PH8), *L. chagasi* (MHOM/BR/82/BA-2,C1 and MHOM/BR/84/Jonas), *L. donovani* (MHOM/Et/67/HU3), *L. infantum* (IPT-1), *L. major* (LTM p-2), *L. tropica* (1063C), *Trypanosoma cruzi* (MHOM/CH/00/Tulahuen C2) and *T. brucei* (TREU 667) were used and have been previously described (see, Burns et al., *Proc. Natl. Acad. Sci. U.S.A.* 90:775–779, 1993). Promastigotes and epimastigotes were cultured in axenic media. *L. chagasi* and *L. amazonensis* amastigotes were obtained from spleens of Syrian hamsters and footpads of BALB/c ByJ mice respectively, and purified as described in Burns et al., *J. Immunol.* 146:742–748, 1991.

Genomic DNA was prepared, digested with enzymes which cut both within (Pst I and Not I) and outside of LbeIF4A (BamH I, EcoR I, EcoR V, Hind III, Pvu II, and Sst I), separated on 0.7% agarose gel and blotted onto Nytran (nylon) membrane, as described in Sambrook et al., *Molecular Cloning: A Laboratory Manual*, Cold Spring Harbor Laboratory Press, New York, 1989. A restriction fragment comprising a ~0.94 kb fragment (nucleotides 143 to 1083) of the coding region of LbeIF4A was radiolabeled by the random priming method (see, Feinberg and Vogelstein, *Anal. Biochem.* 137:266–268, 1984) and blots were hybridized overnight at 65° C. Blots were washed twice at 65° C. for 20 minutes with each of 2×, 0.5× and 0.2×SSC containing 0.1% SDS. *L. braziliensis* genomic DNA contained at least two copies of LbeIF4A as exemplified by the presence of two hybridizing bands in the BamH I and Pvu II lanes (FIG. 1).

The same figure also illustrates the cross-species conservation between the eIF4A homologue of *L. braziliensis* and other Leishmania species. Two major Pst I hybridizing fragments were detected in all other Leishmania species tested with members of the L. donovani complex (L. chagasi, L. donovani, and L. infantum) showing identical hybridization patterns. LbeIF4A also cross-hybridizes with the more distantly related parasite T. cruzi but not T. brucei under stringent hybridization conditions. These data show extensive cross-species conservation of the Leishmania eIF4A homologue.

Example 3

Preparation of LbeIF4A

This example illustrates the expression and purification of the ~45 kDa LbeIF4A antigen gene product. The 45 kDa recombinant antigen of the genomic clone pLeIF.1 (i.e., the antigen lacking the N-terminal 48 residues) was purified from 500 ml of IPTG-induced cultures. The inclusion bodies were isolated and sequentially washed in 10 ml TNE (50 mM Tris, pH 8.0, 100 mM NaCl and 10 mM EDTA) containing 2, 4 and 8M urea. Fractions containing solubilized recombinant antigen (usually the 4 and 8M urea supernatants) were pooled, dialyzed against Tris-buffered saline (TBS) and concentrated by precipitation with 30% ammonium sulfate. Purification to homogeneity was accomplished by preparative SDS-PAGE electrophoresis, followed by excision and electroelution of the recombinant antigens. All antigens used in our studies had less than 10 pg/ml or 1 ng/mg protein endotoxin in a Limulus amebocyte assay performed by Immunex Corp., Seattle, Wash. These amounts of endotoxin are insignificant for cytokine induction and/or adjuvant activity.

The recombinant antigen was used to immunize a rabbit for the production of a polyclonal anti-serum. An adult rabbit (New Zealand White; R & R Rabbitry, Stanwood, Wash.) was immunized by subcutaneous immunization with 100 μg of purified LbeIF4A in incomplete Freund's adjuvant (IFA, GIBCO, Grand Island, N.Y.) together with 100 μg of muramyl dipeptide (adjuvant peptide, Calbiochem-Novabiochem Corp., La Jolla, Calif.), followed by a boost four weeks later with 100 μg of the recombinant antigen in IFA alone. Three weeks later, the rabbit was boosted intravenously with 25 μg of LbeIF4A in saline and serum was collected one week later.

Figure 2:
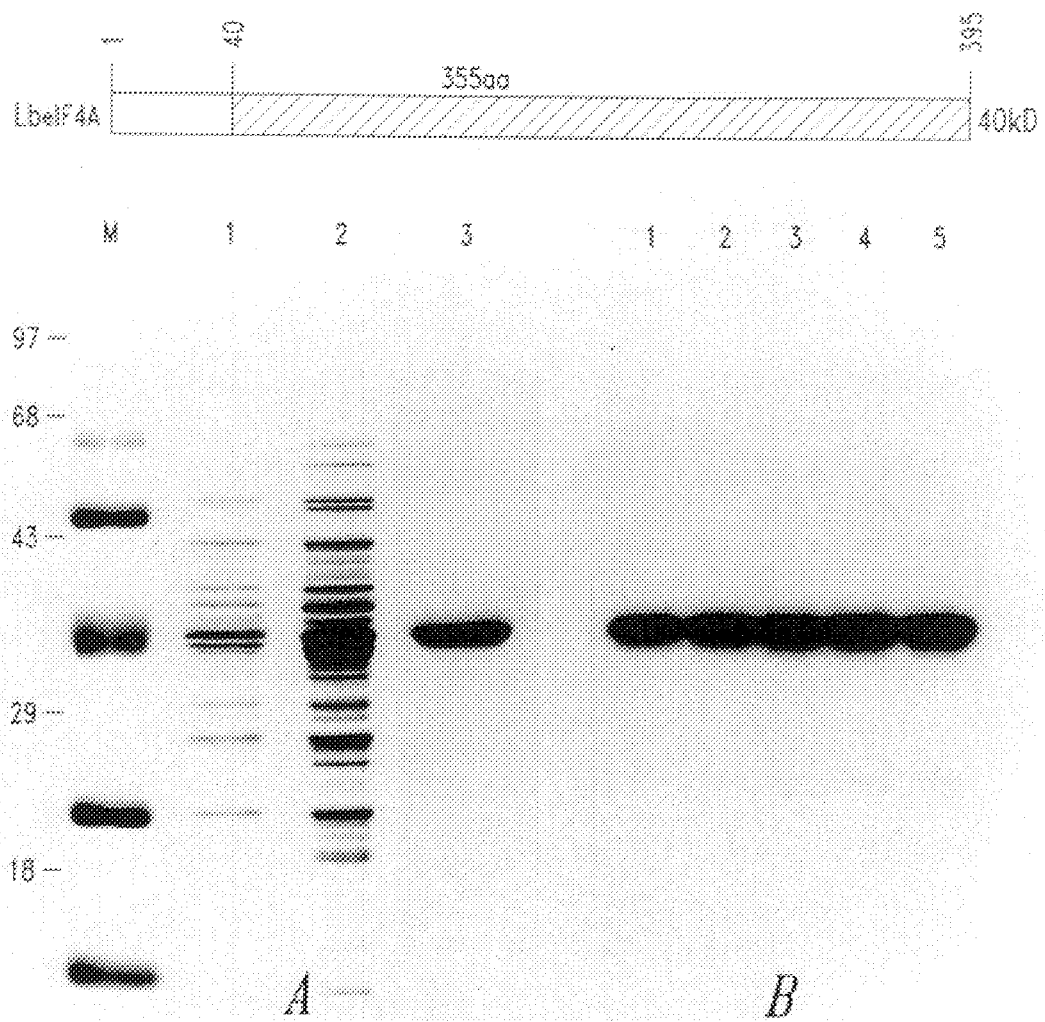
FIG. 2 shows the results of an immunoblot analysis which demonstrates that LbeIEF4A immune rabbit serum reacts with one dominant protein species of size ~45 kDa in different Leishmania species.

Immunoblots of L. braziliensis lysates from promastigotes harvested during the early-, mid-, or late-log phases or following a temperature shift of the culture from 22°–35° C. were subsequently performed with the polyclonal rabbit anti-serum as a probe (FIG. 2). Panel A of FIG. 2 shows the immunoblot analysis of molecular weight markers (lane M), E. coli lysates from uninduced (lane 1) and induced (lane 2) cultures, and the purified recombinant antigen (lane 3). Panel B of FIG. 2 shows the immunoblot analysis of L. braziliensis promastigote lysate (lane 1), L. chagasi promastigote lysate (lane 2), and L. amazonensis promastigote (lane 3) or amastigote (lane 4) lysate.

Parasite and mammalian cell lysates were prepared by freeze/thaw lysis of pellets in SDS sample buffer without glycerol and β-mercaptoethanol. Insoluble material was separated from the supernatant by centrifugation at 10K rpm in a microfuge. Protein concentrations were determined using the Pierce BCA protein assay kit. Five to 10 μg of parasite or cell extracts or 0.5 to 1.0 μg of recombinant antigens were separated on 12.5% SDS-PAGE and transferred electrophoretically to nitrocellulose membranes. Reactivities of the antisera were assessed as previously described (Skeiky et al., J. Exp. Med. 176:201–211, 1992) using [$^{125}$I]-Protein A, followed by autoradiography.

The rabbit anti-serum detected one dominant protein species of size ~45 kD. The relative intensities of the 45 kD eIF4A homologue were similar for all the lysates analyzed, thus suggesting that this antigen is constitutively expressed during the early- to mid-log growth phase of the parasite or following a temperature transition that mimics the intracellular amastigote stage. This is unlike members of the Leishmania heat-shock protein family whose products are upregulated following a temperature transition from 22°–35° C. The pre-immune rabbit serum did not react with the parasite lysates.

Example 4

Preparation of Monoclonal Antibodies that Bind to LbeIF4A

This example illustrates the preparation of monoclonal antibodies against LbeIF4A. Preparations of purified recombinant LbeIF4A or transfected cells expressing high levels of LbeIF4A, may be employed to generate monoclonal antibodies against LbeIF4A using conventional techniques, such as those disclosed in U.S. Pat. No. 4,411,993. Such antibodies may be used to interfere with LbeIF4A activation of PBMCs, as components of diagnostic or research assays for LbeIF4A, or in affinity purification of LbeIF4A.

To immunize rodents, LbeIF4A immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. Ten days to three weeks days later, the immunized animals are boosted with additional immunogen and periodically boosted thereafter on a weekly, biweekly or every third week immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable, such as inhibition of the elicitation of a Th1 response.

Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma lines thus generated can be screened by ELISA for reactivity with LbeIF4A, for example, by adaptations of the techniques disclosed by Engvall et al. (*Immunochem.* 8:871, 1971) and in U.S. Pat. No. 4,703,004. A preferred screening technique is the antibody capture technique described by Beckman et al., *J. Immunol.* 144:4212 (1990). The hybridoma lines are cloned, for example, by limiting dilution or by cloning in soft agar, to yield a monoclonal cell line. Positive clones are then injected into the peritoneal cavities of syngeneic rodents to produce ascites containing high concentrations (>1 mg/ml) of anti-LbeIF4A monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to LbeIF4A.

Example 5

LbeIF4A Stimulation of PBMC Proliferation

This example illustrates the ability of purified recombinant LbeIF4A to stimulate proliferation of PBMCs from *L. braziliensis*-infected individuals. Peripheral blood was obtained from individuals living in an area (Corte de Pedra, Bahia, Brazil) endemic to *L. braziliensis* transmission where epidemiological, clinical, and immunological studies have been performed for over a decade. Diagnosis of the patients was made by clinical findings associated with at least one of the following: isolation of parasite from lesions, a positive skin test with Leishmania lysate or a positive serological test.

Peripheral blood was collected and PBMCs isolated by density centrifugation through Ficoll™ (Winthrop Laboratories, New York). For in vitro proliferation assays, $2-4 \times 10^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of [$^3$H] thymidine for the final 18 hours of culture.

Figure 3:
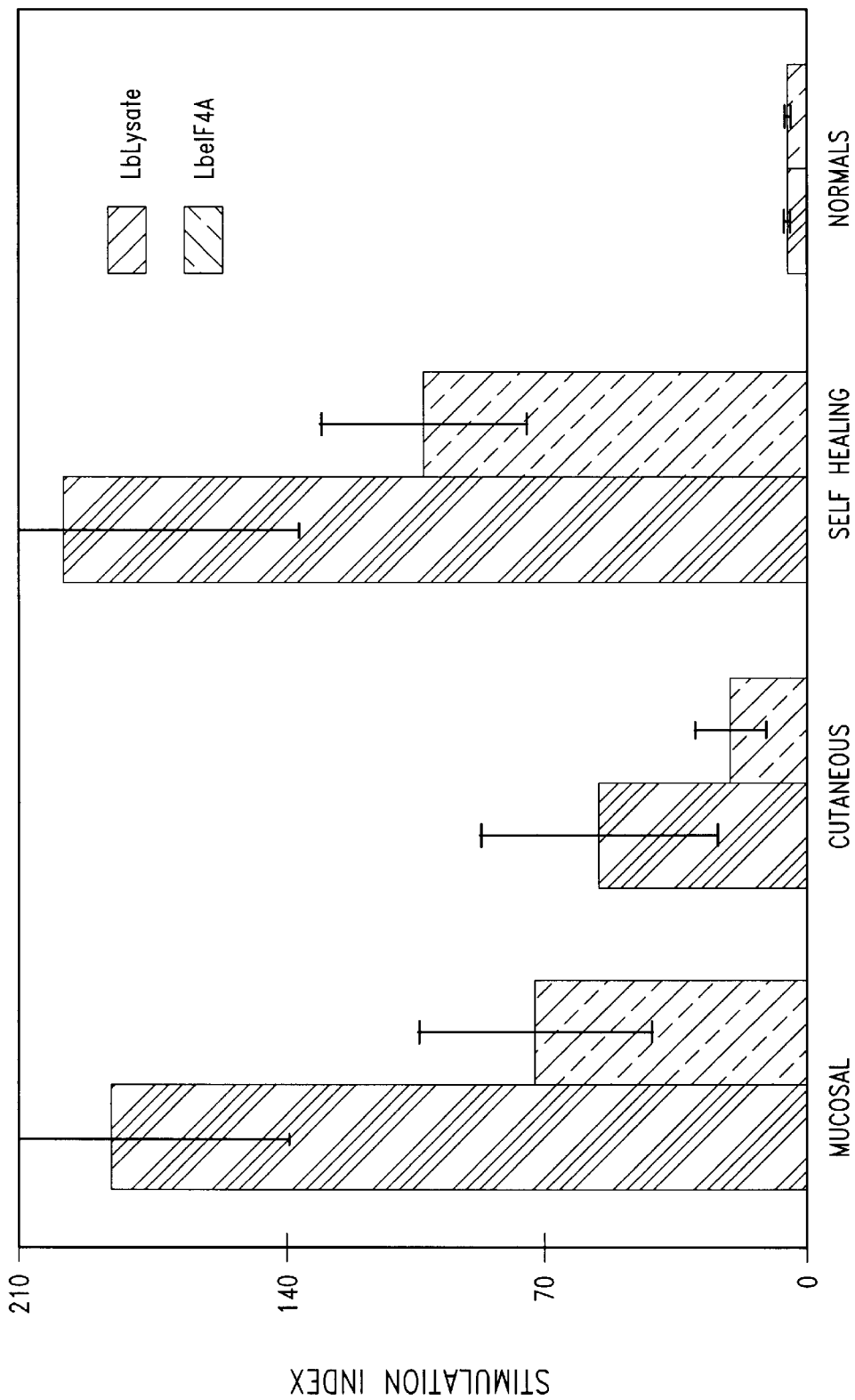
FIG. 3 illustrates the ability of purified recombinant LbeIF4A to stimulate proliferation of PBMCs from *L. braziliensis*-infected individuals.

Data are represented as mean cpm of triplicate cultures and the stimulation index (SI) defined as mean cpm of cultures with antigens/mean cpm of cultures without antigen. As shown in Table I and FIG. 3, PBMCs from most (>70%) mucosal and active or healed cutaneous patients responded to LbeIF4A with a heterogeneous proliferation pattern with stimulation indices to ranging from 12 to 233 and 2 to 64 respectively.

TABLE I

In Vitro Proliferation of PBMCs from *L. braziliensis*-infected Individuals in Response to Parasite Lysate and LbeIF4A Antigens

| | [$^3$H]Tdr Incorporation (Mean cpm (SD) × $10^{-3}$) | | | | |
|---|---|---|---|---|---|
| PATIENTS | MEDIA | LYSATE | S.I. | LbeIF4A | S.I. |
| MUCOSAL | | | | | |
| JV | 0.15 (0.0) | 41.30 (1.3) | 294 | 11.90 (4.8) | 81 |
| SZ | 0.45 (0.1) | 140.60 (7.6) | 308 | 105.90 (5.6) | 233 |
| AB | 0.42 (0.3) | 44.20 (0.5) | 104 | 5.00 (1.3) | 12 |
| NO | 0.38 (0.1) | 52.70 (3.3) | 138 | 12.80 (1.6) | 33 |
| TE | 0.18 (0.0) | 27.40 (1.5) | 150 | 8.80 (0.3) | 48 |
| MB | 0.18 (0.0) | 300.10 (9.4) | 1634 | 41.50 (4.5) | 226 |
| OM | 0.28 (0.0) | 35.40 (3.2) | 124 | 6.90 (2.5) | 24 |
| CUTANEOUS | | | | | |
| AS | 0.22 (0.0) | 19.14 (1.3) | 87 | 14.30 (2.3) | 64 |
| JP | 0.25 (0.0) | 55.63 (8.6) | 218 | 4.40 (0.3) | 17 |
| VS | 0.17 (0.0) | 0.26 (0.0) | 1.5 | 0.3 (0.0) | 2 |
| RJ | 0.10 (0.0) | 0.32 (0.2) | 3.0 | 1.5 (0.6) | 15 |
| 3A | 0.16 (0.0) | 0.77 (0.1) | 4.7 | 2.5 (0.2) | 16 |
| AD | 4.20 (1.0) | 4.01 (1.0) | 0.0 | 14.1 (2.2) | 3.5 |
| HN | 0.36 (0.0) | 4.73 (1.7) | 13 | 4.69 (1.7) | 13 |
| DIFFUSE CUTANEOUS | | | | | |
| VAL | 0.22 (0.0) | 0.51 (0.3) | 2.0 | 2.12 (0.2) | 9.0 |
| SELF-HEALING CUTANEOUS | | | | | |
| GS | 0.21 (0.0) | 19.70 (4.4) | 94 | 41.50 (2.8) | 198 |
| MS | 0.09 (0.0) | 0.60 (0.1) | 6.5 | 5.10 (2.1) | 57 |
| AH | 0.11 (0.0) | 59.60 (7.1) | 519 | 9.60 (4.7) | 83 |
| DJ | 0.12 (0.0) | 0.20 (0.1) | 1.6 | 19.00 (6.7) | 151 |
| HS | 0.12 (0.0) | 27.10 (2.0) | 225 | 12.40 (2.7) | 103 |
| MCT | 0.38 (0.0) | 130.30 (14) | 340 | 6.20 (1.5) | 16 |
| NORMAL | | | | | |
| LV | 0.14 (0.0) | 0.19 (0.0) | 1.4 | 0.71 (0.1) | 4.0 |
| VV | 0.18 (0.0) | 0.31 (0.1) | 1.7 | 0.28 (0.1) | 1.5 |
| N3 | 0.14 (0.0) | 0.36 (0.1) | 2.6 | 0.27 (0.1) | 1.9 |
| N4 | 0.59 (0.1) | 2.00 (0.3) | 3.8 | 0.56 (0.0) | 1.0 |

In general, the stimulation indices were higher with PBMCs from mucosal individuals. PBMCs from some mucosal patients responded to LbeIF4A with stimulation indices comparable to those observed with parasite lysate. Interestingly, in some patients with cutaneous leishmaniasis, the proliferative responses to LbeIF4A were higher than those elicited by parasite lysate. In contrast to mucosal and cutaneous patients, PBMCs from all six individuals with self healing cutaneous leishmaniasis proliferated in response to LbeIF4A with stimulation indices (16–198) comparable to those of mucosal individuals. PBMCs from two of the self healing individuals (MS and DJ), had responses that were significantly higher than those obtained with parasite lysate. Cells from normal uninfected individuals were only marginally stimulated by LbeIF4A.

Example 6

LbeIF4A Stimulation of Cytokine mRNA Expression in PBMCs

This example presents an analysis of cytokine mRNA expression patterns of PBMCs from patients with confirmed cases of *L. braziliensis* infection. For cytokine mRNA analysis, 0.5 to 1 ml of PBMCs were cultured at $1-2 \times 10^6$ cells/ml with or without 10 μg/ml of the LbeIF4A antigen lacking the N-terminal 48 residues of SEQ ID NO:2 (as described in Example 3) for 48 and 72 hours. The supernatants and cells were harvested and analyzed for cytokine mRNAs by polymerase chain reaction (PCR). For cytokine mRNA PCR analysis, total RNA was isolated from the PBMCs using the acid guanidium thiocyanate-phenol-chloroform extraction method, as described by Chomczynski and Sacchi (*Anal. Biochem.* 162:156–159, 1987). Complementary DNA (cDNA) was synthesized using poly (dT) (Pharmacia) and AMV reverse transcriptase (Bethesda Research Laboratories, Gaithersburg, Md.) in a final volume of 20 μl. cDNA samples were brought to 200 μl with water.

Following normalization to β-actin, 12 to 20 μl of diluted cDNA were amplified by PCR using Taq polymerase (Perkin-Elmer Cetus, Norwalk, Conn.) with 0.2 μM of the respective 5' and 3' external primers in a reaction volume of 50 μl. The conditions used were: denaturation at 94° C. (1 minute for β-actin, IL-2, and IL-4; 45 sec for IFN-γ and 30 sec for IL-10), annealing at 55° C. (1 minute for β-actin, IL-2, and IL-4; 30 sec for IL-10) or 60° C. for 45 sec for IFN-γ and elongation at 72° C. We verified that our PCR conditions were within the semi-quantitative range by initially performing serial dilutions of the cDNAs and varying the number of cycles used for PCR. In all subsequent experiments, 30 cycles were used in the amplification reactions for β-actin, IL-2, IL-4, and IFN-γ. In the case of IL-10 PCR, 25 cycles were used.

The primer pairs used and the PCR conditions were from published information; β-actin, IL-2, IL-4 and IFN-γ (Ehlers et al., *J. Exp. Med.* 173:23–36, 1991) and IL-10 (Viera et al., *Proc. Natl. Acad. Sci. U.S.A.* 88:1172–1176, 1991). The nucleotide sequences for the 5' and 3' oligonucleotide primers, respectively, were as follows: (1) β-actin, TGACGGGGTCACCCACACTGTGCCCATCTA (SEQ ID NO:5) and CTAGAAGCATTGCGGTGGACGATG-GAGGG; (SEQ ID NO:6) (2) IL-2, ATGTACAGGATGCA ACTCCTGTCTT (SEQ ID NO:7) and GTCAGTGT-TGAGATGATGCTTTGAC; (SEQ ID NO:8) (3) IL-4, ATGGGTCTCACCTCCCAACTGCT (SEQ ID NO:9) and CGAACACTTTGAATATTTCTCT CTCAT; (SEQ ID NO:10) (4) IFN-γ, ATGAAATATACAAGTTATATCTTG-GCTTT (SEQ ID NO:11) and GATGCTCTTCGACCTC-GAAACAGCAT; (SEQ ID NO:12) (5) IL-10, TCT-CAAGGGGCTGG GTCAGCTATCCCA (SEQ ID NO:13) and ATGCCCCAAGCTGAGAACCAAGACCCA (SEQ ID NO:14).

Probes were obtained using plasmids containing the human sequences IL-2, IFN-γ and IL-4 (Lewis et al., *Proc. Natl. Acad. Sci. U.S.A.* 85:9743–9747, 1988) and β-actin (no. 65128; American Type Culture Collection, Rockville, Md.), which were digested with Hind III/EcoR I, EcoR I, Sac I/Hind III, and EcoR I respectively. Human IL-10 cDNA was cloned by PCR from mitogen-stimulated PBMCs from normal donors using oligonucleotide primers designed to amplify a 535 base pair fragment spanning the entire coding region of human IL-10 (Lewis et al., *Proc. Natl. Acad. Sci. U.S.A.* 85:9743–9747, 1988). The cDNA was subcloned into pBluescript and digested with BamH I/EcoR I. After separation on 1% agarose gels, insert DNA fragments were excised, electroeluted, and purified. Radiolabeled $^{32}$P-probes were prepared by the random priming method.

PCR products were analyzed by electrophoresis on 1.5% agarose gels, transferred to nylon membranes, and probed with the appropriate $^{32}$P-labeled DNA insert. Hybridizations were at 55° C. overnight. Post hybridization washes were at 55° C. for 20 minutes twice each with 2×, and 1×SSC containing 0.2% SDS.

Figure 4A:
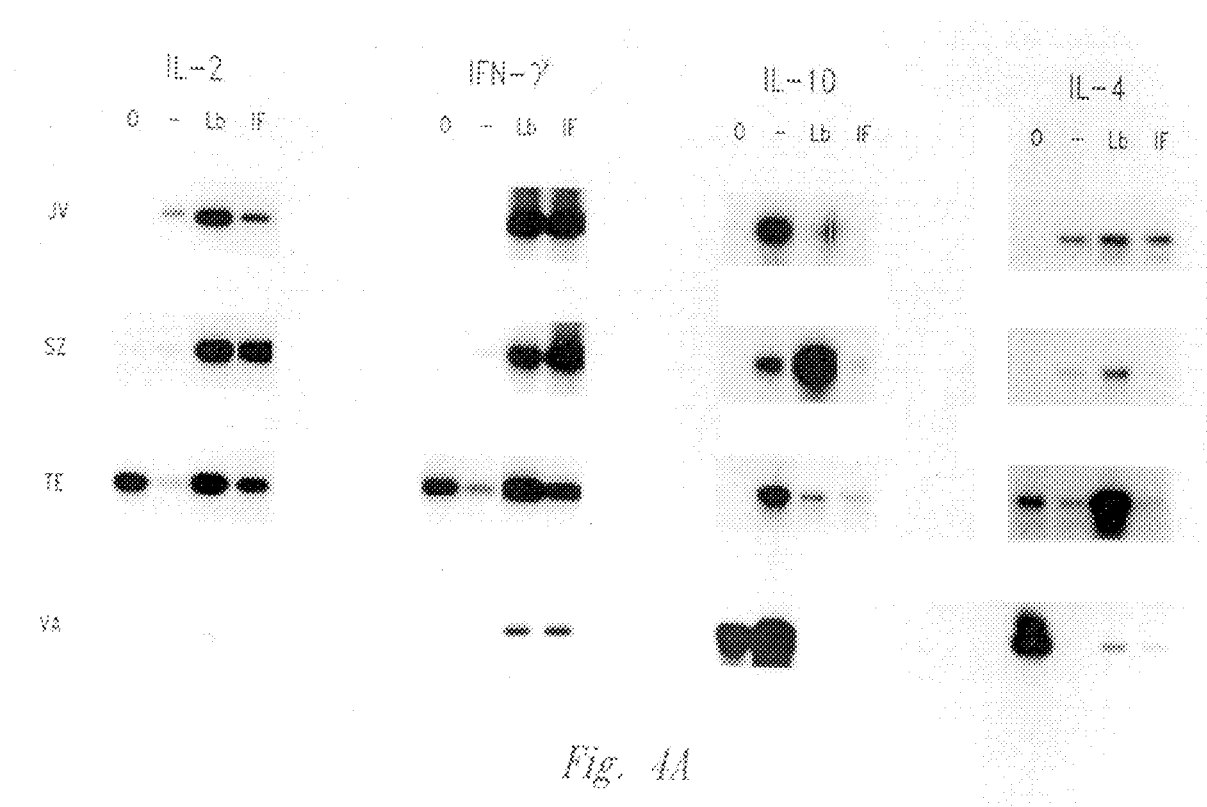
FIGS. 4A and 4B present the results obtained by analysis of cytokine mRNA expression patterns of PBMCs from patients with confirmed cases of *L. braziliensis* infection.
Figure 4B:
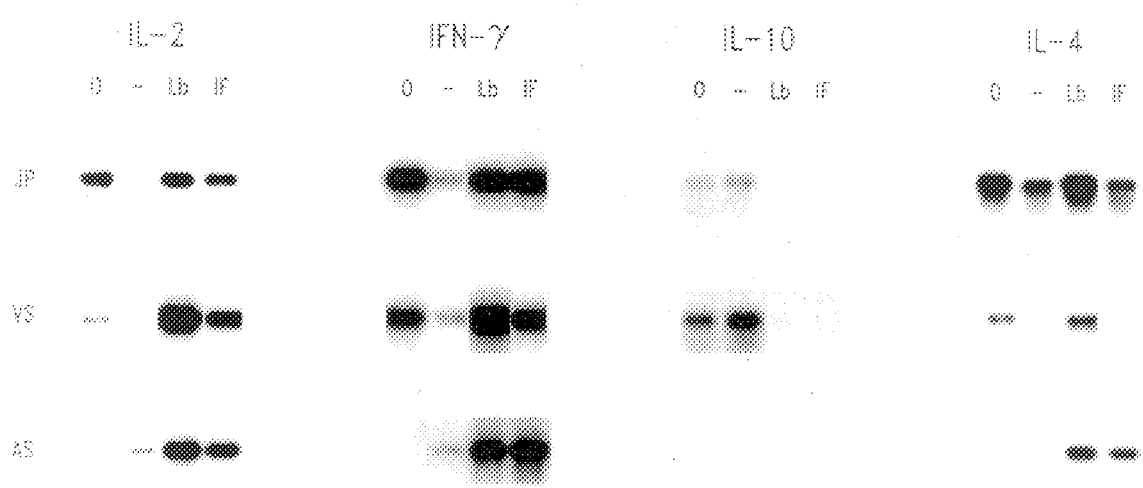

The results of these analyses are presented in FIGS. 4A and 4B. PCR cytokine analyses were performed with cells prior to culturing (lanes 0), following culturing in the absence of antigen (lanes –), or following culturing in the presence of 10 μg/ml *L. braziliensis* lysate (lanes Lb) or in the presence of 10 μg/ml LbeIF4A (lanes IF). FIG. 4A shows the PCR results of cytokine mRNA for three of the six mucosal patients' PBMCs analyzed (JV, SZ, and TE) and one patient (VA) with *L. amazonensis* infection, manifested as diffuse cutaneous leishmaniasis (DCL). In three of the six mucosal patients (TE, FIG. 4A; NO and EO, not shown), PBMCs not cultured in vitro had detectable levels of mRNA for IFN-γ and IL-4, as well as IL-2 (patients TE and EO). IL-10 mRNA was not detected in the "resting" PBMCs from any of the mucosal patients. However, following in vitro culturing in the absence of antigen stimulation, the synthesis of IL-10 mRNA was upregulated in most of the mucosal PBMCs analyzed. In addition, the levels of cytokine mRNAs detected in the "resting" PBMCs of patients TE, NO, and EO, decreased to background levels.

Parasite lysate stimulated the expression of mRNAs of the Th1 cytokines IFN-γ and IL-2 as well as that of the Th2 cytokine IL-4 (in three of the six patients). Increased IL-10 mRNA was detected in one of the patients' PBMCs (SZ) following culture with the parasite lysate. Both LbeIF4A antigen and parasite lysate elicited the production of mRNA of IFN-γ and IL-2 from all mucosal patient PBMCs with LbeIF4A eliciting an exclusive Th1 cytokine profile. In fact, LbeIF4A downregulated the synthesis of IL-10 mRNA detected in the cultured PBMCs of most mucosal patients prior to antigen stimulation. Interestingly, as with the case of using PBMCs from mucosal patients, LbeIF4A also downregulated the synthesis of IL-10 mRNA in the DCL patient VA.

In general, the levels of mRNAs for IFN-γ and IL-2 increased from undetectable amounts prior to antigen stimulation to readily visual levels following antigen stimulation in ethidium bromide stained gels. However, mRNA for the cytokines IL-4 and IL-10, were only detected following radioactive probing of the resolved PCR products, indicating low abundance of these cytokine messages.

Similar PCR analysis was performed on PBMCs derived from cutaneous patients (FIG. 4B). The fresh PBMCs from three (VS, JP and CA (not shown)) of the four patients analyzed revealed high levels of mRNAs for both the Th1 (IFN-γ and (IL-2) and Th2 (IL-4 and IL-10) cytokines examined. mRNAs for IFN-γ and IL-2, but not for IL-10 and IL-4, were detected in the fresh PBMCs of the fourth (AS) cutaneous patient. Therefore, in contrast to mucosal patients, patients with cutaneous leishmaniasis have IL-10 mRNA, in addition to IL-4, IL-2, and IFN-γ, in their fresh PBMCs. Interestingly, while the mRNAs for IL-2 and IFN-γ were reduced to barely detectable levels following the in vitro culturing of PBMCs in the absence of antigen, those for IL-10 remained either unaffected or increased. Therefore, in cutaneous patients, the spontaneous levels of IL-10 mRNA is either stable or their PBMCs continue to synthesize IL-10 mRNA in the absence of antigen stimulation. The observation of such a response for cutaneous leishmaniasis patients can be exploited to differentiate individuals who are predisposed to developing chronic cutaneous leishmaniasis from those who will experience self healing lesions.

All cutaneous patients tested responded to LbeIF4A antigen as well as to the parasite lysate by upregulating the synthesis of mRNAs for IL-2 and IFN-γ and, in two of four patients (VS and AS), the level of IL-4 mRNA also increased following stimulation with parasite lysate. In the three patients (VS, JP and CA) with detectable spontaneous levels of IL-10 mRNA, LbeIF4A as well as the parasite lysate down-regulated the expression of IL-10, mRNA.

The cytokine mRNA profiles of PBMCs from patients with self-healing CL were similar to those of ML patients in that (a) except for one individual with detectable levels of IL-10 mRNA, fresh PBMCs from three of four patients analyzed had detectable levels of IL-2, IFN-γ and IL-4, but little or no IL-10 mRNA; (b) IL-10 mRNA was upregulated after culture of PBMCs without antigen, whereas those of IL-2, IFN-γ and IL-4 decreased to background levels; and (c) leishmanial lysate stimulated the expression of a mixed Th1/Th2 cytokine profile, whereas LbeIF4A elicited increased mRNA expression of only the Th1-type cytokines and downregulated the expression of IL-10 mRNA in the cultured PBMCs of most self-healing individuals (not shown).

Example 7

LbeIF4A Stimulation of Cytokine Secretion in PBMCs

This example presents the supernatant levels of secreted cytokines of PBMCs from *L. braziliensis*-infected individuals following stimulation with LbeIF4A antigen lacking the N-terminal 48 residues of SEQ ID NO:2 (as described in Example 3) or parasite lysate. Aliquots of the PBMC supernatants were assayed for IFN-γ, TNF-α, IL-4, and IL-10. IFN-γ was quantitated by a double sandwich ELISA using mouse anti-human IFN-γ mAb (Chemicon, Temucula, Calif.) and polyclonal rabbit anti-human IFN-γ serum. Human IFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml. IL-10 was measured using a rat anti-human IL-10 mAb (PharMingen, San Diego, Calif., Cat. #18551D) to "capture" secreted IL-10 and a biotinylated rat antihuman IL-10 mAb (PharMingen San Diego, Calif., Cat. #18562D) for detection of bound IL-10 with streptavidin conjugated horse radish peroxidase and ABTS as substrate. A standard curve was obtained using human rIL-10 (kindly provided by DNAX Research Institute, Palo Alto, Calif.), ranging from 30 pg to 2 ng/ml.

Figure 5:
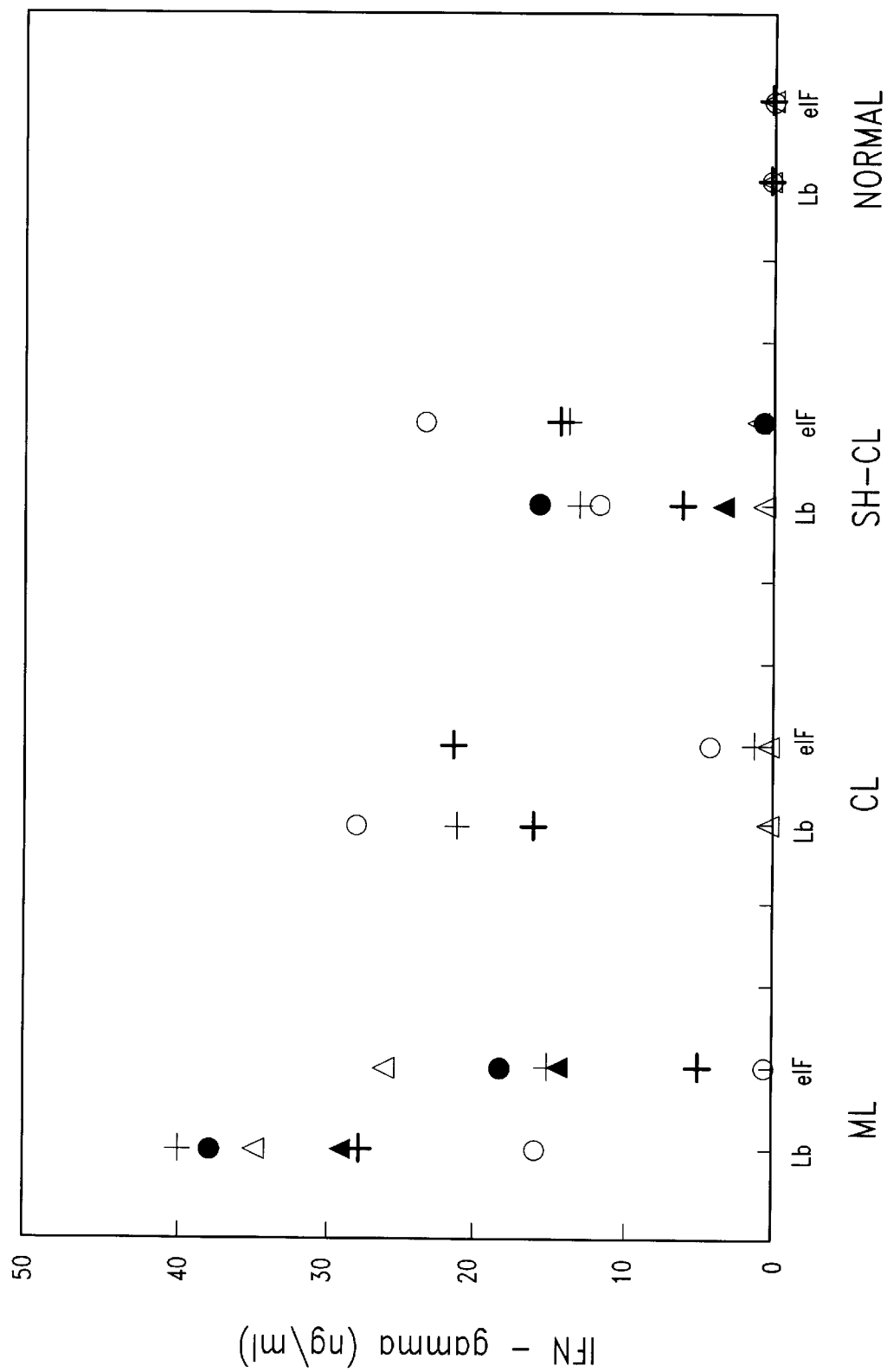
FIG. 5 illustrates the supernatant levels of secreted IFN-γ from PBMCs from *L. braziliensis*-infected individuals following stimulation with LbeIF4A or parasite lysate.
Figure 6:
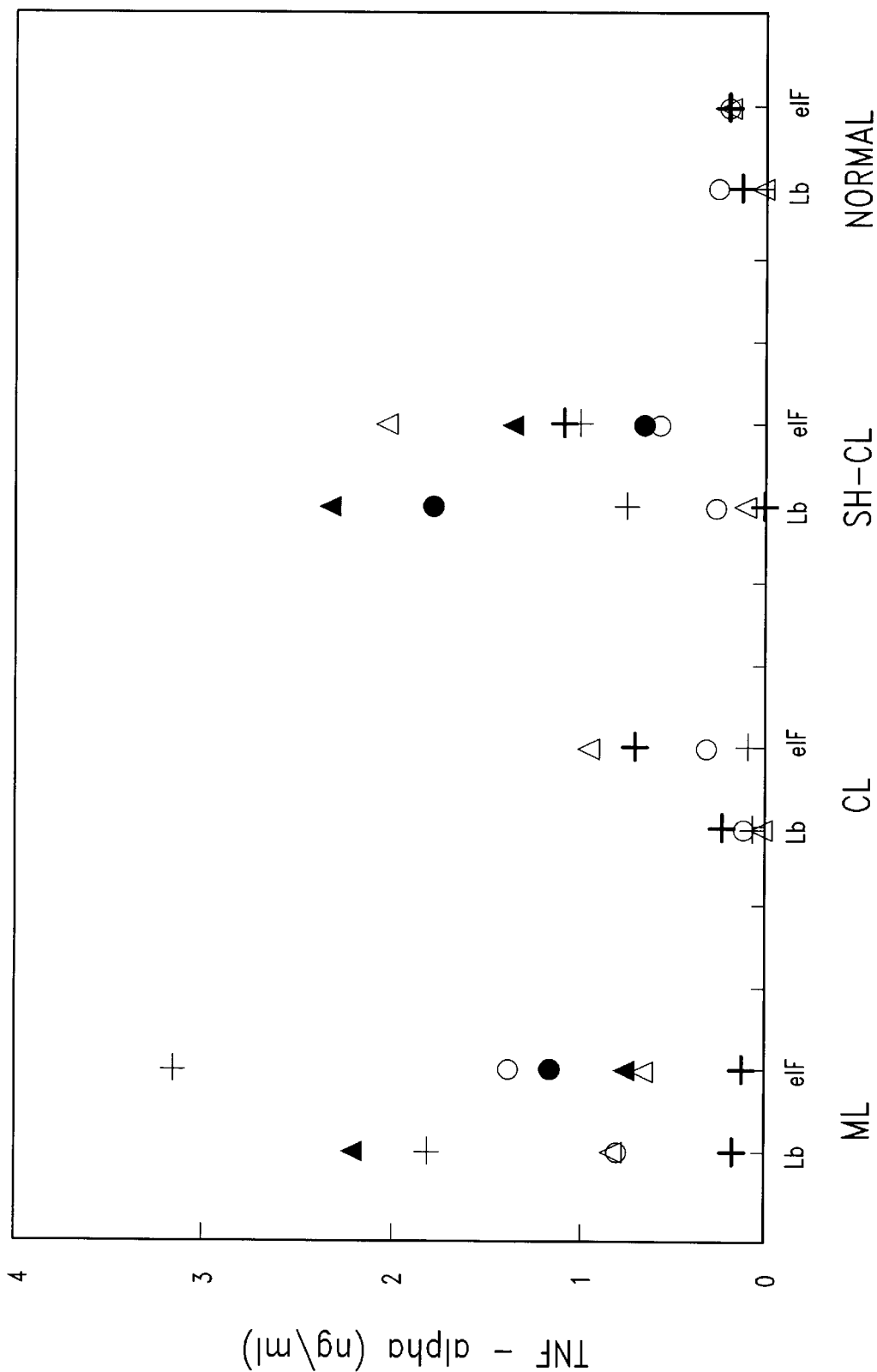
FIG. 6 shows the levels of TNF-α detected in the supernatants of PBMCs from *L. braziliensis*-infected individuals following stimulation with LbeIF4A or parasite lysate.

Cells from all three patient groups (i.e., mucosal, cutaneous and self-healing cutaneous) secreted IFN-γ and TNF-α following stimulation with either 10 μg/ml LbeIF4A antigen or 10 μg/ml parasite lysate (FIGS. 5 and 6). Similarly, LbeIF4A stimulated PBMCs from patients with *L. tropica* infection (Desert Storm Patients) to proliferate and secrete IFN-γ (not shown). The levels of both IFN-γ and TNF-α detected in the supernatants of patient PBMCs were significantly higher than those from uninfected controls. In the absence of antigen stimulation, only PBMCs from mucosal patients (five of six) produced detectable levels of supernatant TNF-α (60 to 190 pg/ml). Little or no IL-4 or IL-10 was detected in any of the supernatants analyzed (not shown), indicating levels below the detection limit of the ELISA assay employed. By comparison, leishmanial lysate also stimulated PBMCs to secrete IFN-γ and TNF-α and, in some patients, IL-10 was also detected (not shown). Taken together, the results demonstrate that LbeIF4A stimulated a predominant Th1 cytokine profile in PBMCs from *L. braziliensis*-infected individuals, whereas parasite lysate stimulated a mixed Th1/Th2 cytokine profile.

The levels of TNF-α detected in the supernatants of patient PBMCs from mucosal and self-healing individuals following antigen stimulation were higher than those from cutaneous patients (FIG. 6). PBMCs from four of five mucosal patients (JV, SZ, AB, and MB) had supernatant levels of TNF-α (0.80 to 2.20 ng/ml) higher than those detected in cultures of PBMCs from uninfected controls following stimulation with parasite lysate. Similarly, the same PBMCs were stimulated by LbeIF4A to produce supernatant levels of TNF-α with values ranging from 0.66 to 3.14 ng/ml. Compared to uninfected controls, PBMCs from three (GS, HS, and MCT) out of six self-healing individuals analyzed produced higher levels of TNF-α in response to parasite lysate, and all six (GS, MS, AH, DJ, HS, and MCT) out of six self-healing individuals analyzed produced higher levels of TNF-α in response to LbeIF4A. The levels of TNF-α produced by PBMCs from cutaneous leishmaniasis patients in response to parasite lysate were comparable to uninfected controls. However, LbeIF4A stimulated PBMCs in three of these patients (RJ, AD and JS) to produce TNF-α. Such patients may be in the process of developing acute cutaneous leishmaniasis.

Example 8

Stimulation of IL-12 Production by LbeIF4A

This example shows that LbeIF4A stimulates PBMCs from *L. braziliensis*-infected individuals, as well as PBMCs or cultured human macrophages, adherent PBMCs, from the blood of normal donors and the human myeloid leukemia cell-line THP-1, to secrete IL-12. IL-12 has been shown to play a pivotal immunoregulatory role in the development of cell mediated immunity, generation of Th1 responses and IFN-γ production in intracellular bacterial or parasitic infections. The LbeIF4A polypeptide used was the LbeIF4A antigen lacking the N-terminal 48 residues of SEQ ID NO:2 (as described in Example 3).

IL-12 p40 was measured in cell-free supernatants by RIA (detection limit of 10 pg/ml) using the mAb pairs C11.79/C8.6, as described by D'Andrea et al. (*J. Exp. Med.* 179:1387–1398, 1992). Biologically active IL-12 p70 heterodimer (detection limit 1 pg/ml) was measured as described by Kubin et al. (*Blood* 83:1847–1855, 1994).

Figure 7A:
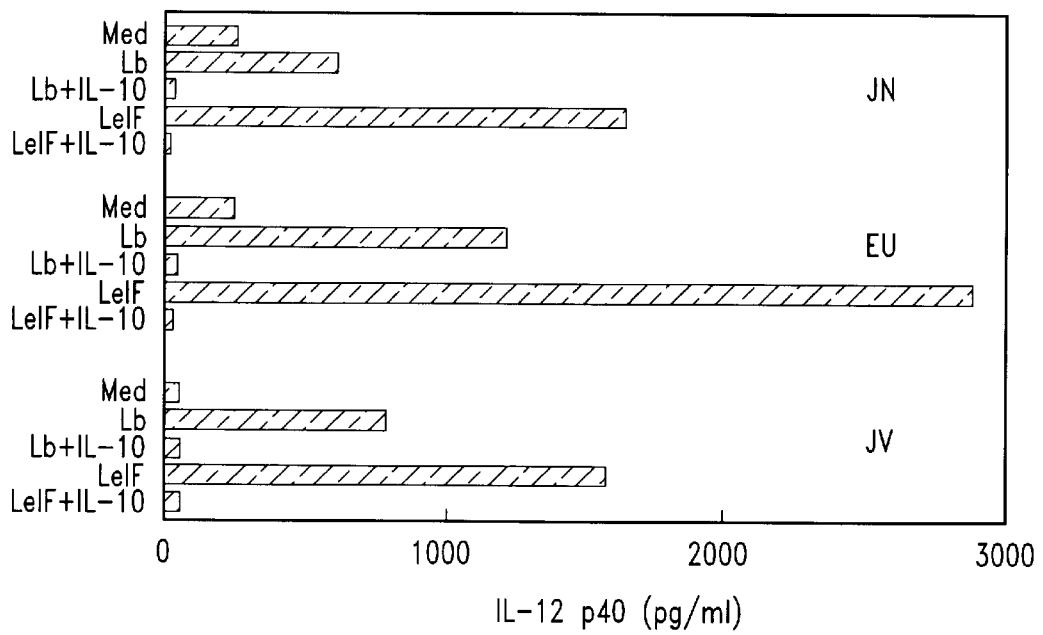
FIG. 7, Panels A–D, shows that LbeIF4A also stimulates patient PBMCs to secrete IL-12 in the cultured supernatant with a magnitude significantly higher than the IL-12 level stimulated by parasite lysate and that IL-10 inhibits this IL-12 production.

FIG. 7A shows that 10 μg/ml LbeIF4A (LeIF) stimulated mucosal patient PBMCs to secrete IL-12 p40 in the cultured supernatant with a magnitude significantly higher than the IL-12 p40 levels observed with 10 μg/ml parasite lysate as antigen (Lb). The amount of IL-12 p40 secreted in the absence of lysate or antigen is also shown (Med). The same figure also shows that 10 μg/ml IL-10 down-regulated the production of IL-12 p40 by patient PBMCs following stimulation with LbeIF4A (LeIF+IL-10) or lysate (Lb+IL-10).

Figure 7B:
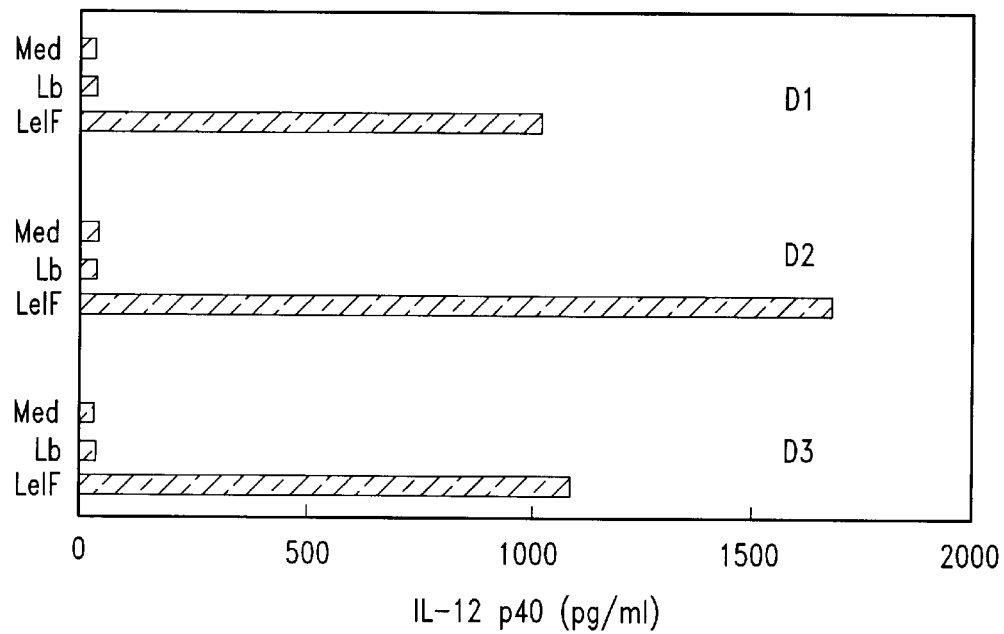

PBMCs from uninfected individuals also produced IL-12 p40 when cultured with LbeIF4A (LeIF, FIG. 7B), although no p40 was detected in response to parasite lysate (Lb). This may suggest a role for IFN-γ in the lysate-induced p40 observed in patient PBMCs, which produced 5–100 fold more IFN-γ than normal PBMCs after antigen stimulation (see FIG. 5).

Figure 7C:
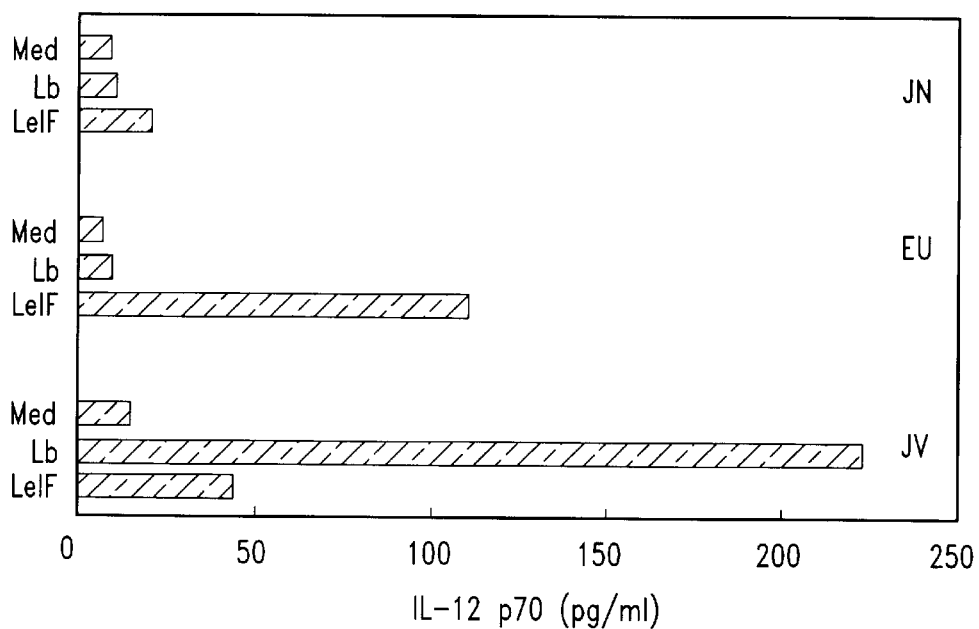
Figure 7D:
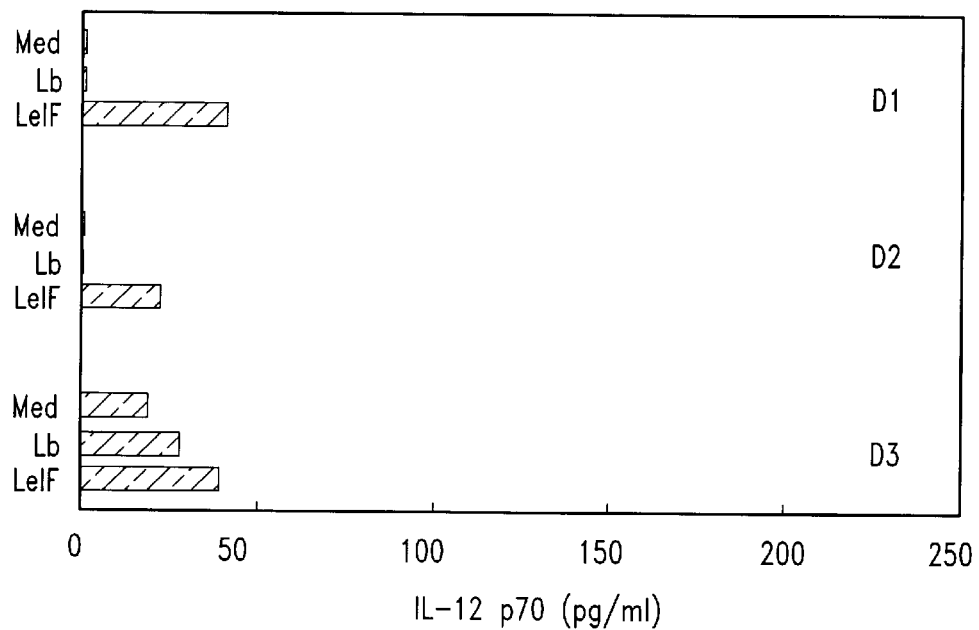

To determine whether the IL-12 p40 observed in antigen-stimulated PBMC cultures reflected biologically active cytokine, IL-12 p70 was also assayed in these cultures (FIGS. 7C and 7D). In general, the p70 production paralleled that of p40, demonstrating that biologically active IL-12 was produced in response to LbeIF4A in both patient and normal PBMCs.

Figure 9A:
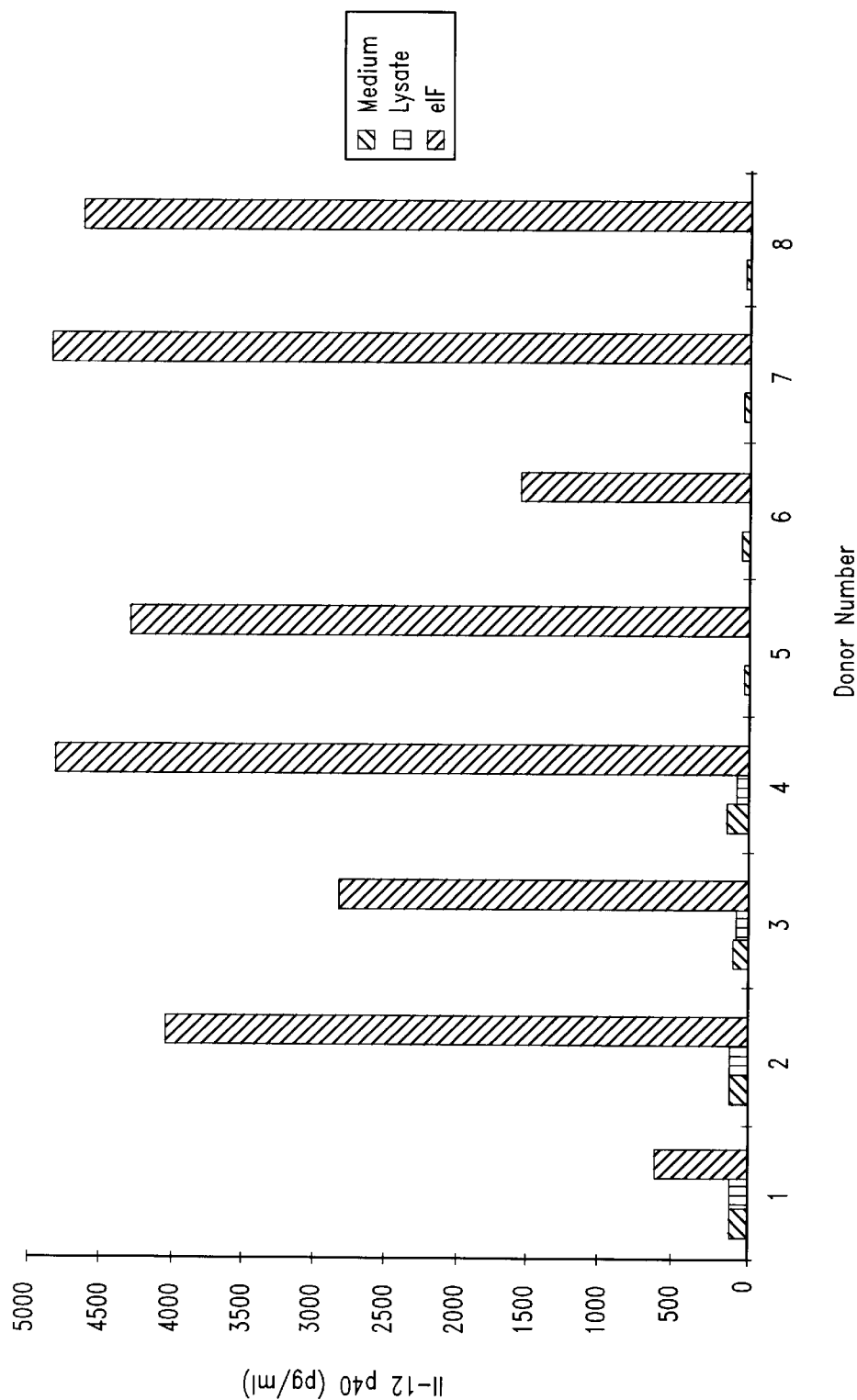
FIGS. 9A and 9B show that LbeIF4A stimulates IL-12 production in cultured human macrophages and adherent PBMCs.
Figure 9B:
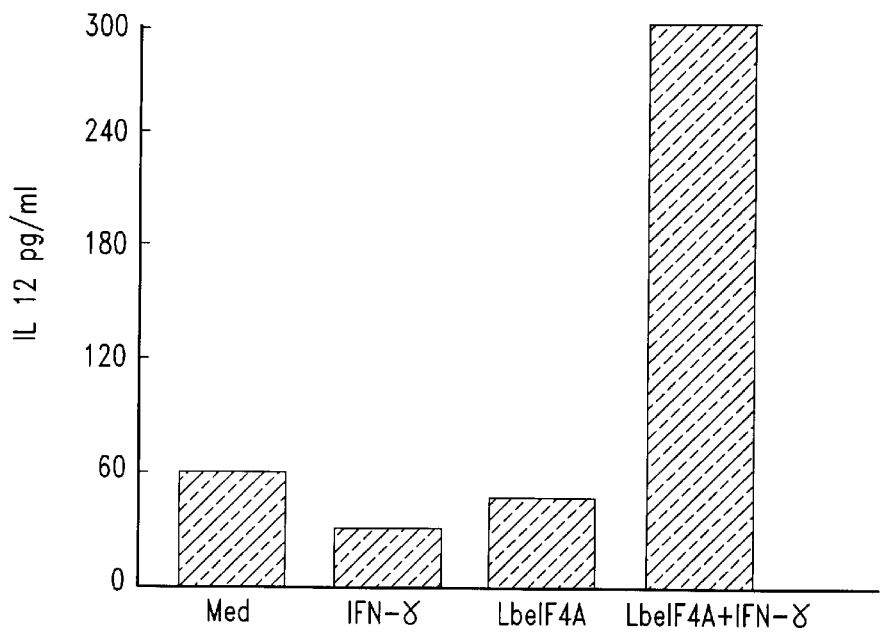

LbeIF4A also stimulates IL-12 production in cultured human macrophages (FIG. 9A) and in adherent PBMCs (FIG. 9B). Adherent cells were prepared from PBMCs separated by Ficoll-hypaque gradient centrifugation from the blood of normal donors. 2×10⁶ PBMCs were cultivated for 2 hours in 500 μl RPMI, 2% human AB serum. Adherent cells were purified by washing the plates 3 times with PBS. Then 500 μl of test medium (RPMI, 2% human AB serum) with the respective stimulus were added (IFN-1000 U/ml, LbeIF4A (Lf) 10 μg/ml). Supernatants were taken after 18 hours.

IL-12 production of adherent PBMCs was measured by a capture bio-assay with 5 day old PHA blast. Briefly, the IL-12 capture antibody C11.5.14 (kind gift of the Wistar Institute) was coated on 96 well plates. Supernatants of the induction experiment and recombinant IL-12, as a standard, were incubated for 4 hours. After several wash steps, 5 day old PHA blasts were added and the proliferation of these blasts was used to determine IL-12 concentrations in supernatants of adherent cells.

Macrophages were generated by cultivating adherent cells (2×10⁶ PBMCs) for 5 days in test medium. Then, the macrophages were washed in PBS and 500 μl RPMI, 2% human AB serum, and 1000 U/mL IFN-γ was added. Macrophages were stimulated with LbeIF4A (10 μg/ml) or cultivated in medium (M) alone. In one set, LbeIF4A control macrophages were incubated with LbeIF4A in 500 μl RPMI, 2% human AB serum, without IFN-γ. Supernatants were taken after 18 hours and used for induction of IL-12 dependent proliferation. Briefly, 5 day old blasts were incubated with macrophage supernatants for 2 days. For the last 18 hours, $^3$H thymidine was added. Neutralizing anti-IL-12 polyclonal goat serum (5 μg/ml) was added as indicated.

Figure 10:
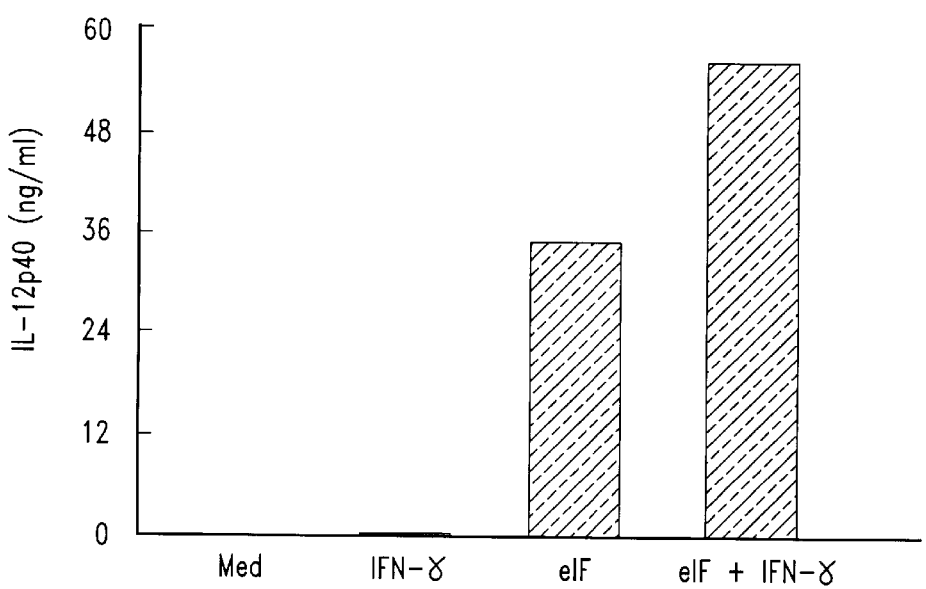
FIG. 10 indicates that LbeIF4A stimulates IL-12 p40 production in the human myeloid leukemia cell-line, THP-1, and synergizes with IFN-γ to stimulate THP-1 cells to secrete IL-12.

In addition, LbeIF4A stimulates IL-12 p40 production in the human myeloid leukemia cell-line, THP-1 (FIG. 10). The cells were cultured at $10^6$ cells/ml for 24–48 hours in Endotoxin-free RPMI medium containing 5% Fetal Bovine serum. 10 μg/ml LbeIF4A synergized with IFN-γ to stimulate THP-1 cells to secrete IL-12 p40. These results indicate the utility of LbeIF4A as vaccine adjuvant.

Example 9

Effect of IL-12 and IL-10 on LbeIF4A Induction of IFN-γ Production

Figure 8A:
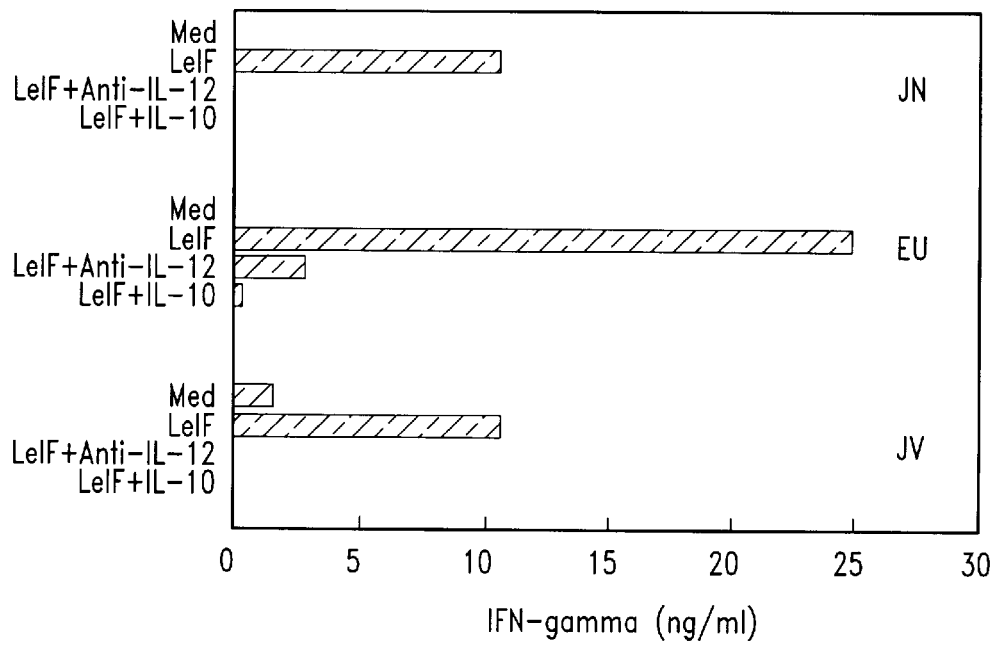
FIG. 8, Panels A and B, demonstrates that in all patient PBMCs tested, IFN-γ production was IL-12 dependent and inhibited by IL-10.
Figure 8B:
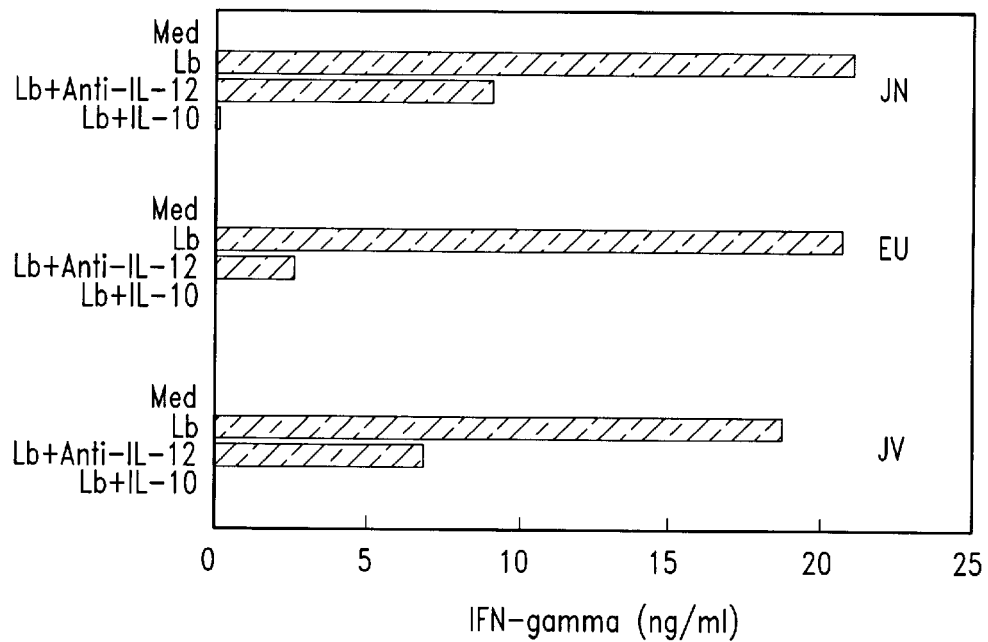

This Example examines the interaction among IL-12, IL-10 and IFN-γ in response to the LbeIF4A polypeptide lacking the N-terminal 48 residues of SEQ ID NO:2 (as described in Example 3). As shown in FIG. 8A, PBMCs from patients with mucosal leishmaniasis were stimulated with 10 μg/ml LbeIF4A in the absence (LeIF) or presence of 10 ng/ml anti-IL-12 (LeIF+Anti-IL-12), or IL-10 (LeIF+IL-10), and the cultured supernatants were assayed for IFN-γ secretion. Both anti-IL-12 mAb and IL-10 abrogated the production of LbeIF4A-induced IFN-γ secretion. However, anti-IL-12 mAb only partially decreased the production of IFN-γ after stimulation with leishmanial lysate (FIG. 8B). These results show that IFN-γ production is IL-12 dependent, and is inhibited by IL-10, whereas the production of IL-12 is regulated by both IFN-γ dependent and independent pathways.

Example 10

LbeIF4A Stimulation of a TH1 Profile in Mice

Figure 11A:
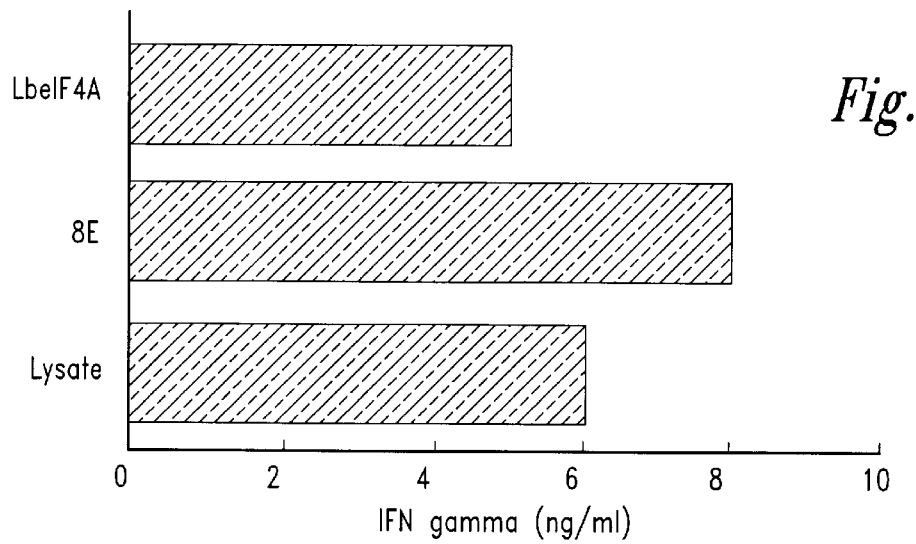
FIG. 11 presents results that indicate that lymph node cells of mice primed with LbeIF4A proliferate and secrete an almost exclusive Th1 cytokine profile.
Figure 11B:
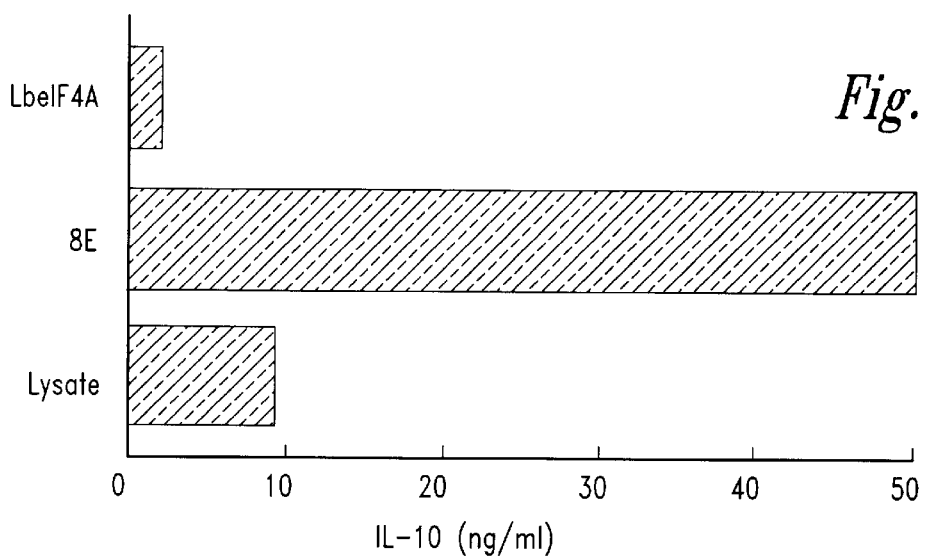
Figure 11C:
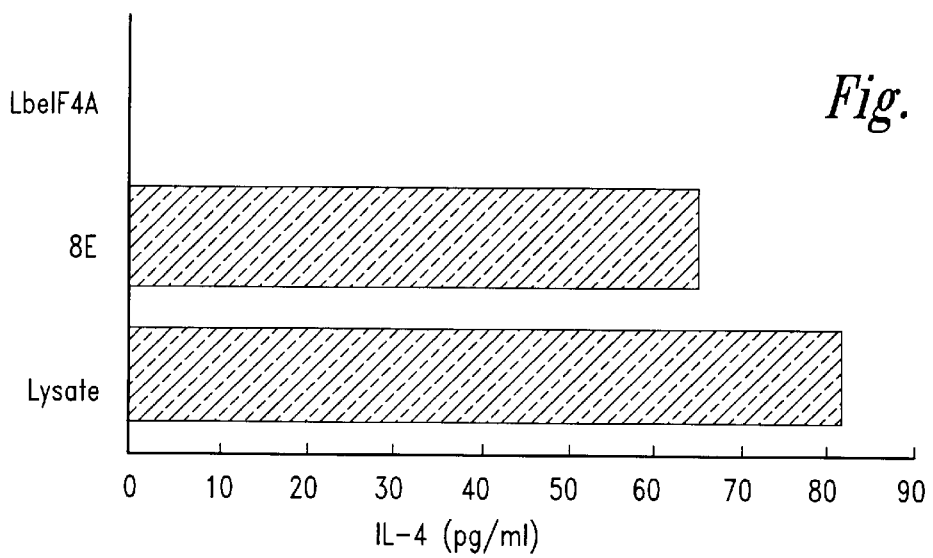

This example demonstrates that the LbeIF4A polypeptide lacking the N-terminal 48 residues of SEQ ID NO:2 (as described in Example 3) stimulates a dominant Th1 cytokine profile in BALB/c mice. The animals were primed with either LbeIF4A or 8E (the C-terminal portion of the *L. braziliensis* mitochondrial hsp70, which stimulates patient PBMCs to produce high levels of IL-10) using quilA or CFA as adjuvants. Ten days after priming, lymph node (LN) cells were restimulated in vitro with the recombinant antigens and the supernatant cultures were analyzed for secreted cytokines. The results (FIG. 11) show that LN cells of mice primed with LbeIF4A proliferated and secreted an almost exclusive Th1 cytokine (IFN-γ) following challenge with LbeIF4A using both types of adjuvants. In contrast, LN cells from mice primed with 8E produced a Th0 response or Th1/Th2 type cytokine (with quilA as adjuvant) with a strong bias towards the Th2 cytokines, IL-4, and IL-10 in specific response to challenge with 8E. Similarly, mice primed with parasite lysate produced a mixed cytokine profile, a result that may argue against the use of parasite lysate alone as vaccine candidate (FIG. 11).

Figure 12:
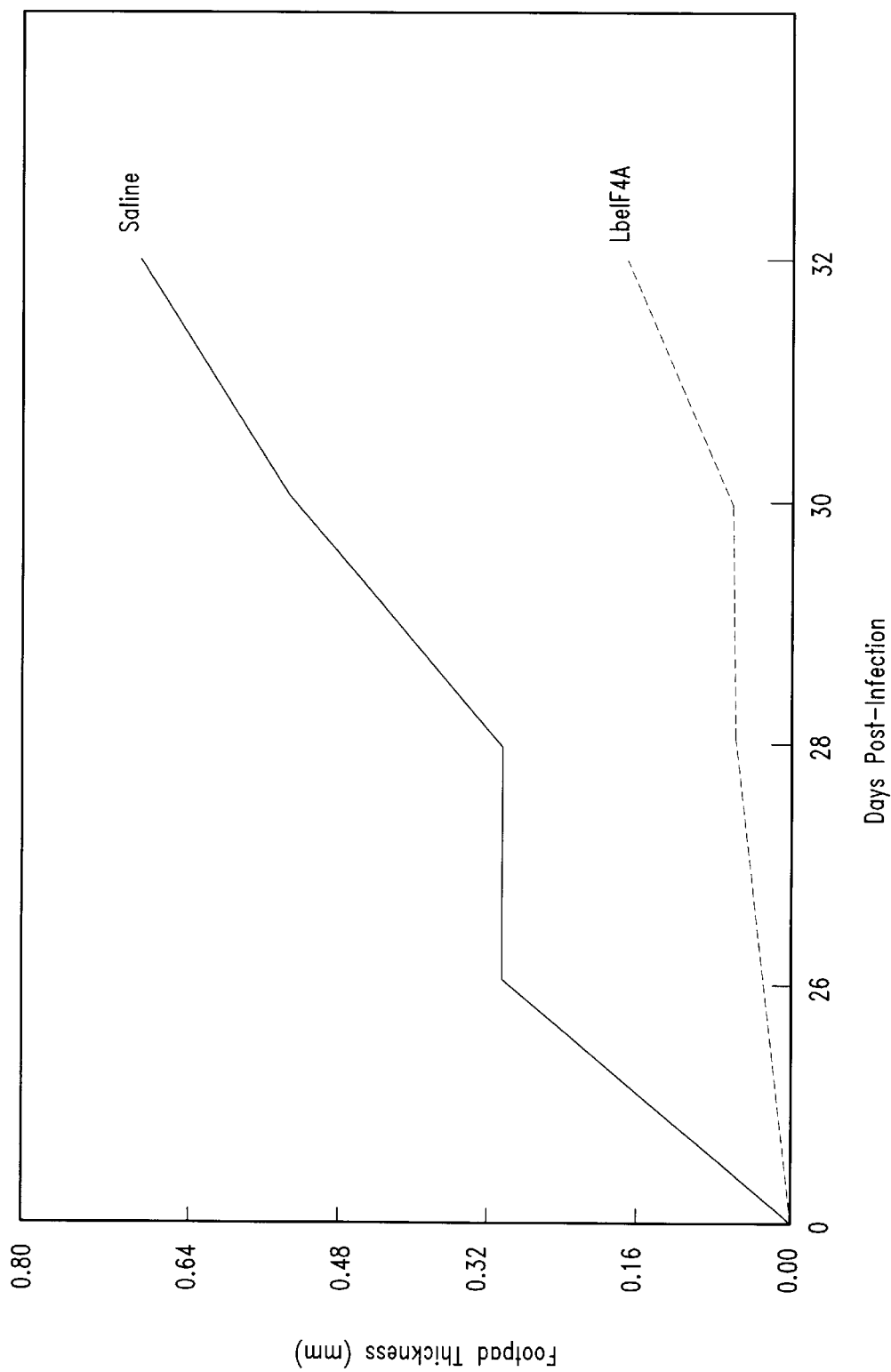
FIG. 12 demonstrates that LbeIF4A provides significant protection against *L. major* infection in an animal model recognized as having relevance to human disease.

These results indicate that LbeIF4A may be used as an adjuvant, as well as a specific T cell vaccine. Because LbeIF4A induced a powerful Th1 response, including the two cytokines most clearly associated with protection in experimental leishmaniasis, IFN-γ and IL-12, we studied the ability of this antigen to protect mice against leishmaniasis. BALB/c mice were immunized once with LbeIF4A with no adjuvant, followed by subcutaneous infection with *L. major* seven days later. Compared to the control group, LbeIF4A provided significant protection against *L. major* infection (FIG. 12). Thus a heterologous antigen derived from *L. braziliensis* can confer some protection to *L. major* infection, suggesting that, at least some of the "protective" epitopes are conserved between the two parasites.

Example 11

Preparation of LmeIF4A

This example illustrates the appropriation of new variant of LbeIF4A from *Leishmania major*.

A cDNA expression library was constructed with polyA$^+$ RNA of *L. major* using the ZAP-cDNA unidirectional cloning kit (Stratagene, La Jolla, Calif.). Approximately 500,000 pfu was screened with a radio-labeled DNA probe comprising nucleotides 258 to 1188 of SEQ ID NO. 1. Post-hybridization washes were at 55° C. with 0.5×SSC containing 0.1% SDS. This resulted in the identification of a clone containing an approximately 2.5 kb insert (LmeIF4A). Excision of the pBSK (−) phagemid sequences was carried out according to the manufacturer's protocols. Overlapping clones were generated from the cDNA insert by exonuclease III and sequenced by the Taq dye terminator.

The approximately 2.7 kb cDNA insert of LmeIF4A was found to contain the entire coding sequence, as well as the 5' spliced leader and 3' flanking sequences. A fragment containing the entire coding sequence of LmeIF4A was amplified by PCR using 5' and 3' specific oligonucleotides. The 5' oligonucleotide contained an Nde I restriction site preceding the ATG initiation site. When cloned into the Nde I site of the pET vector (Novagen, Madison, Wis.), the first amino acid of the protein was the initiation code (Met) of the non-fusion recombinant LmeIF4A. Non-fusion full-length rLmeIF4A was produced in *E. coli*, using the pET plasma vector and a T7 polymerase expression system (Novagen, Madison, Wis.). The inclusion bodies were isolated and sequentially washed twice in 10 ml of TNE (50 mM TRIS, pH 8.0, 100 mM NaCl, 10 mM EDTA) containing 2, 4, and 8M urea. The 8M urea fraction containing a recombinant antigen was applied to a preparative SDS-PAGE gel. Recombinant LmeIF4A was purified either by electroelution from the preparative gel or by HPLC. The final product had negligible levels of bacterial endotoxin, as determined by Limulus assay.

Partial sequence analysis of the LmeIF4A cDNA indicated substantial homology (at the nucleotide and amino acid level) (SEQ ID NOS:3 and 4) to the antigen isolated from *L. braziliensis* (i.e., greater than 90% amino acid sequence identity).

Example 12

Elicitation of Antigen-Specific CTL Response

This example illustrates the elicitation of a specific CTL response against soluble ovalbumin using LmeIF4A, prepared as described above.

C57BL/6 mice (H-2$^b$) were immunized once with 30 μg of soluble ovalbumin (Sigma, St. Louis, Mo.), either alone (ova alone) or in combination with 50 μg of LmeIF4A encapsulated in poly-lactide-glycolide beads (Southern Research Institute, Birmingham, Ala.) (Lmeif/PLG). Groups of mice were also immunized with LmeIF4A encapsulated in PLG beads (ova plus Lmeif/PLG) or PLG alone. The size of beads used for the experiment was in the range of 1 to 10 μm.

Three weeks after immunization, mice were sacrificed and the spleens removed. To generate effector cells, spleen cells were prepared and stimulated in vitro with the ova expressing EG7.ova cells, after irradiation (20,000 rad) for five days. The EG7.ova cell line was generated by transfecting the EL4 thymoma cell line (H-$2^b$) (Infectious Disease Research Institute, Seattle, Wash.) with the ova cDNA-containing plasmid under the control of β-actin as described (Moore et al., Cell 54:777–785 (1988)).

Figure 13:
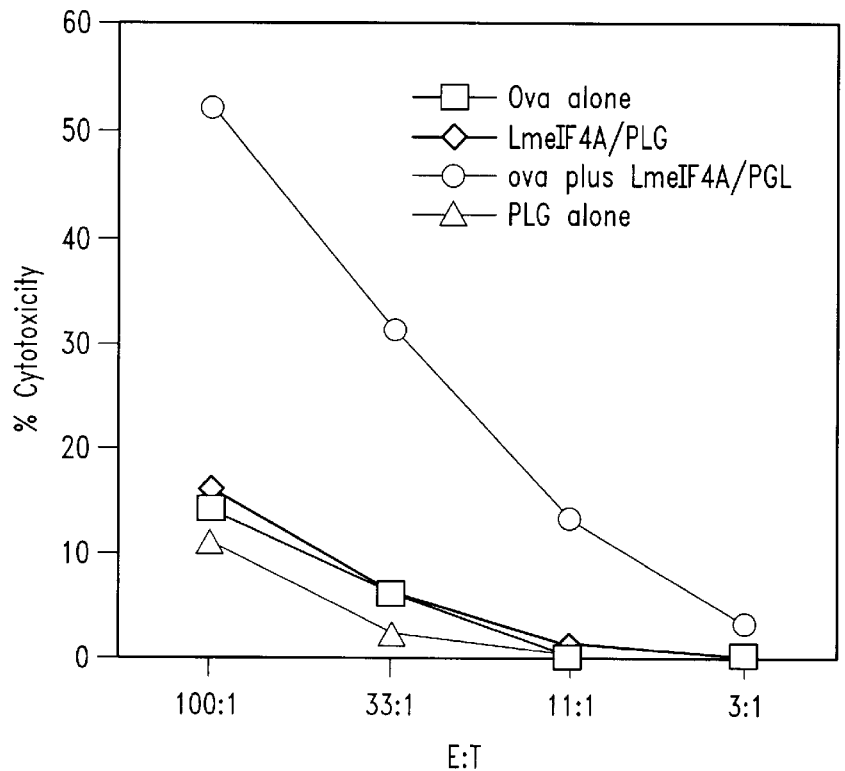
FIG. 13 illustrates the elicitation of anti-ovalbumin CTL using a representative LmeIF4A polypeptide.

Priming was assessed by the presence of effectors capable of lysing $^{51}$Cr labeled EG7.ova, without lysing $^{51}$Cr labeled non-transfectant parental EL4 cells. The results are shown in FIG. 13, and are expressed as % cytotoxicity as a function of effector to target cell ratio. These results demonstrate that mice immunized with soluble ovalbumin in combination with LmeIF4A show an excellent CTL response which killed target cells specifically. No specific CTL elicitation could be detected in mice immunized with either LmeIF4A, PLG or soluble ovalbumin alone.

Example 13

Stimulation of Trinitrophenol-specific Antibodies

This example illustrates the enhancement of anti-trinitrophenol (TNP) antibodies using LmeIF4A.

Figure 14:
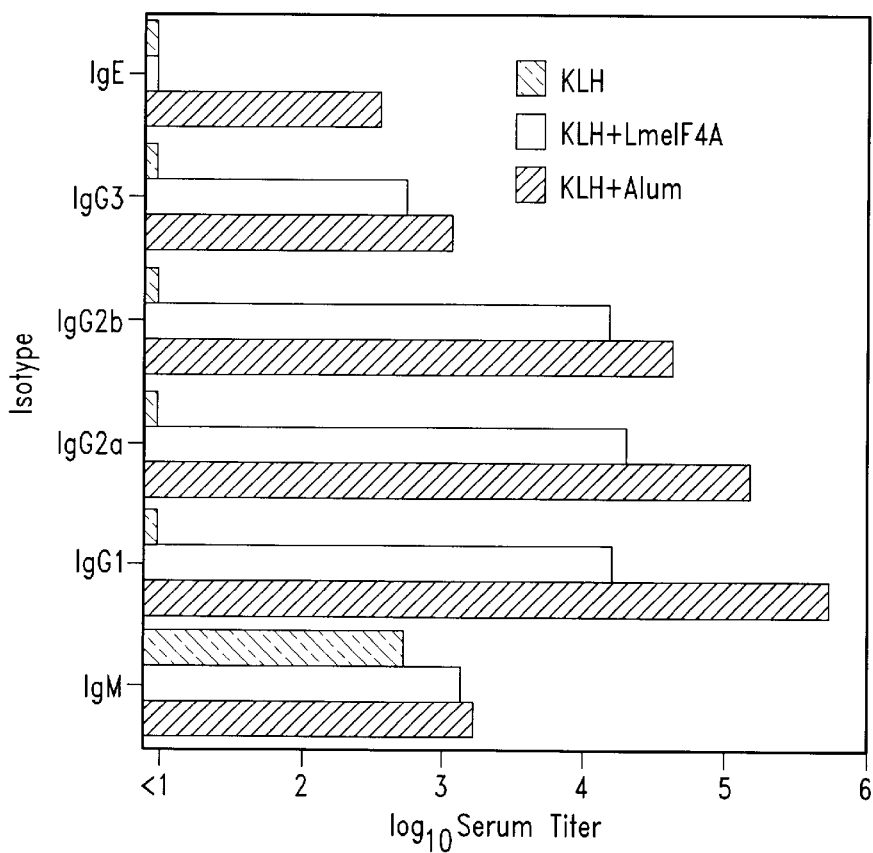
FIG. 14 illustrates the use of a representative LmeIF4A polypeptide as an adjuvant for the induction of antibodies specific for trinitrophenol.

C57BL/6 mice were immunized (day 0) intraperitoneally with 3 μg TNP-KLH combined with either alum, LmeIF4A (75 μg) or with saline. The mice were bled on day 10, boosted (same as primary) on day 21 and bled on day 26. The sera were tested for TNP specific, isotype specific antibody responses by enzyme-linked immunosorbant assay (ELISA). Data are expressed, in FIG. 14, as the log of the dilution of each antiserum that gave a 50 percent of maximum OD in each ELISA, as calculated by linear regression analysis.

These results show a significant enhancement of antibody response by LmeIF4A, as compared to immunization with antigen alone. Of particular interest, no noticeable increase in IgE, the antibody class most associated with the Th2 response, was found. In addition, primary IgM and IgG antibody responses were enhanced after a single injection of TNP-KLH (3 μg) with LmeIF4A (75 μg), as described above.

Example 14

Enhancement of Production of MUC-1 Specific Antibodies

This example illustrates the use of LmeIF4A to enhance the production of MUC-1 specific antibodies.

C57BL/6 mice were immunized with human tumor antigen MUC-1 in various combinations with LmeIF4A. Groups included mice immunized with soluble MUC-1 with or without soluble LmeIF4A and MUC-1 immobilized on PLG beads with or without soluble LmeIF4A. For MUC-1/PLG experiments, two separate bead sizes were used. One batch of beads were used for 1–10 μm in size while the other ranged from 40–100 μm. Ten, twenty and thirty days after immunization, mice were bled and the sera were tested for the presence of MUC-1 specific antibodies (IgG and IgM). The sera were also tested for the presence of μ, γ2a, γ2b and γ1 isotypes.

Figure 15:
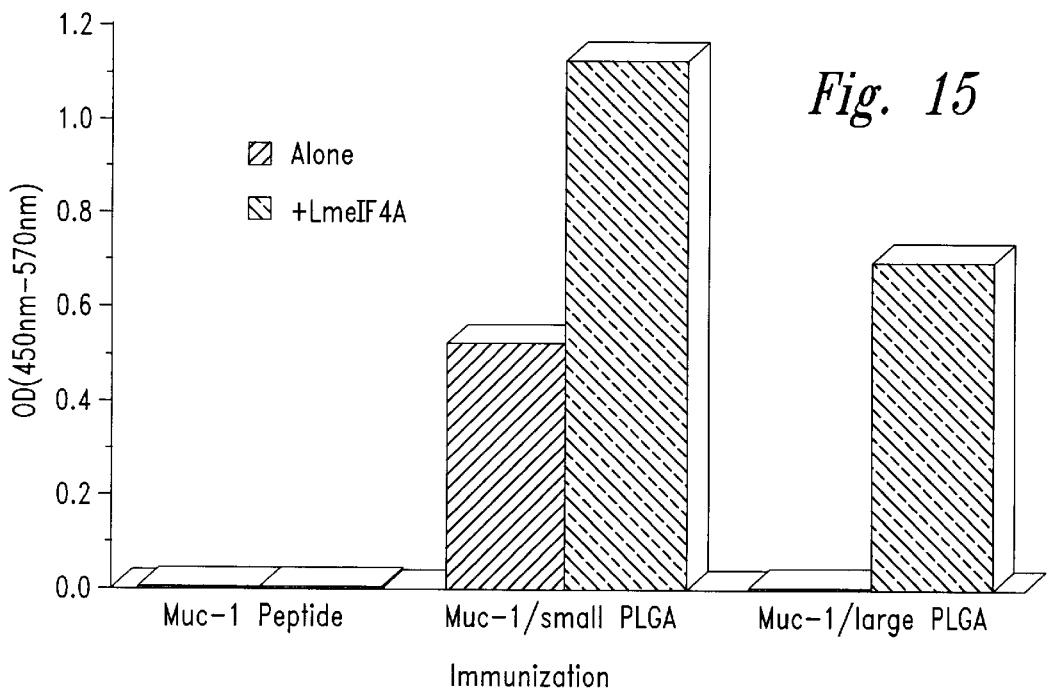
FIG. 15 shows the enhancement of anti-MUC-1 antibody production by a representative LmeIF4A polypeptide.

The results, shown in FIG. 15, demonstrate that, while one immunization with the MUC-1 or MUC-1 plus LmeIF4A antibody response, LmeIF4A significantly enhanced the antibody response when MUC-1 was encapsulated in PLG beads. MUC-1 in small PLG beads induced strong anti-MUC-1 responses deductible as early as 10 days after the first immunization and the addition of LmeIF4A to the preparation further enhanced the antibody response. One immunization with MUC-1 in large PLG beads did not produce any detectable anti-MUC-1 antibodies within 10 days of immunization, but an amplified response was observed in mice immunized with MUC-1 in large PLG beads in combination with LmeIF4A. The isotype distribution of anti-MUC-1 antibodies consisted of IgM, IgGγ2a, IgGγ2b, and IgGγ1 with no IgE response detected.

Example 15

Enhancement of CTL Activity in Cultured Cells

This example illustrates enhancement of specific CTL activity by LmeIF4A in cultured cells.

Figure 16:
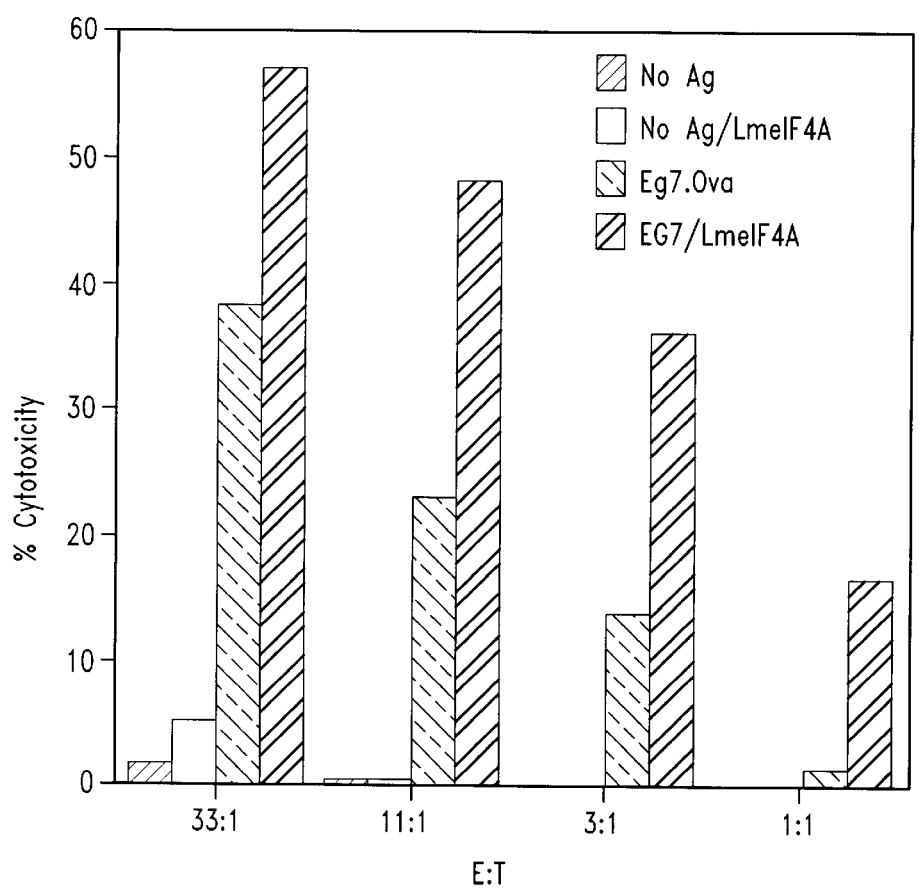
FIG. 16 illustrates the enhancement of specific CTL activity by a representative LmeIF4A polypeptide in cultured cells.

Mice were immunized with 30 μg of soluble ovalbumin or the same concentration of ovalbumin encapsulated in PLG beads. After two weeks, spleen cells were removed from immunized mice and stimulated in vitro with no antigen, LmeIF4A alone (10 μg/ml) irradiated EG7.ova or irradiated EG7.ova plus LmeIF4A at the same concentration. The results are shown in FIG. 16.

These results indicate that ovalbumin/PLG immunized mice can prime ovalbumin-specific CTL in vivo which can be detected by stimulating responder spleen cells with EG7.ova stimulator cells. Furthermore, CTL generation from ovalbumin/PLG primed spleen cells can be substantially augmented by the addition of LmeIF4A (10 μg/ml) to the EG7.ova containing cultures. It should be noted that in the first in vitro culture with EG7.ova or EG7.ova plus LmeIF4A, total mononuclear cell counts did not differ (see Tables 2 and 3 below).

TABLE II

LmeIF4A Enhances CTL Activities Ex Vivo

| Immunized With | Stimulated ex vivo with | Lytic Units (LU)/$10^6$ Mononuclear Cells |
| --- | --- | --- |
| None | No antigen | 0 |
|  | LmeIF4A alone | 0 |
|  | EG7.Ova | 0 |
|  | EG7.Ova plus LmeIF4A | 0 |
| Bead alone | No antigen | 0 |
|  | LmeIF4A alone | 0 |
|  | EG7.Ova | 0 |
|  | EG7.Ova plus LmeIF4A | 0 |
| Ova/bead | No antigen | 0 |
|  | LmeIF4A alone | 0 |
|  | EG7.Ova | 2.5 |
|  | EG7.Ova plus LmeIF4A | 16.6 |

TABLE III

Recovery of Mononuclear Cells from LmeIF4A Containing Cultures

| Immunized With | In Vitro Stimulated With | No. of Cells (LU)/$10^6$ Recovered/$10^7$ Mononuclear Cells Added |
| --- | --- | --- |
| Ova/PLGA | No Antigen | 1.8 |
|  | LmeIF4A alone | 2.4 |
|  | EG7.Ova | 2.52 |
|  | EG7.Ova plus LmeIF4A | 2.88 |
|  | Soluble Ova | 3.2 |
|  | Soluble Ova plus LmeIF4A | 2.6 |

We also evaluated whether LmeIF4A can be used to potentiate and expand antigen specific CTL activities in vitro. CTLs generated from ovalbumin/PLG-immunized mice discussed above were restimulated in vitro with either irradiated EG7.ova plus IL-2 or with EG7.ova plus IL-2 and LmeIF4A. After five days of culture, effector cells were tested against $^{51}$Cr-labelled EL4 cells or EG7.ova cells.

Figure 17:
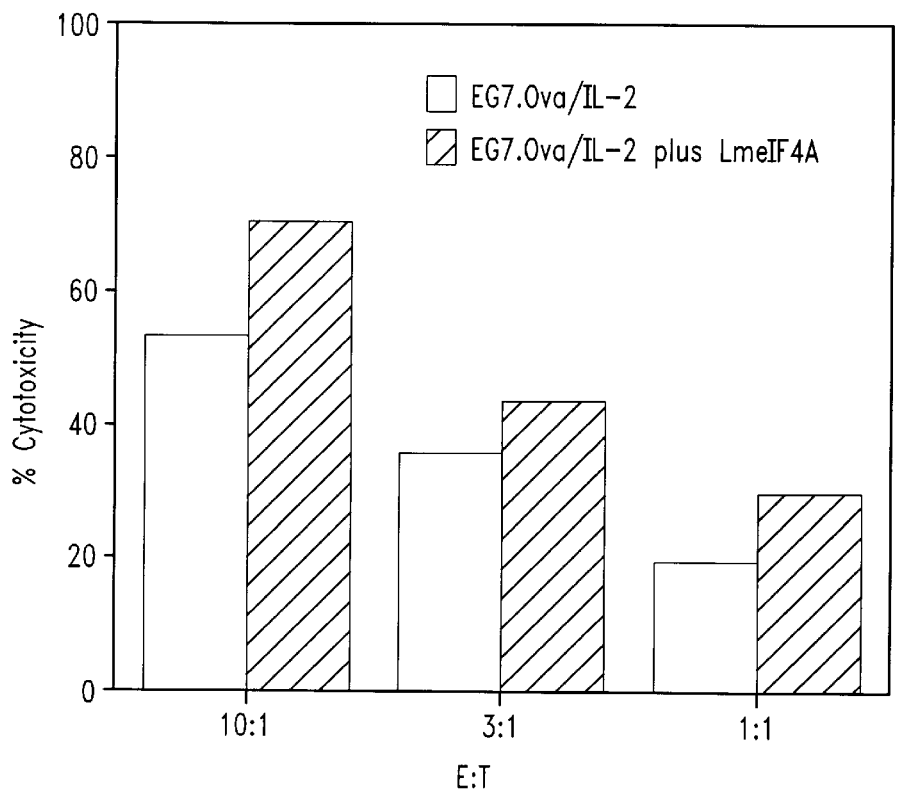
FIG. 17 shows the in vitro stimulation of CTL activity with IL-2, with and without an LmeIF4A polypeptide.

The results, shown in FIG. 17, indicate that ovalbumin-specific CTL restimulated with EG7.ova plus LmeIF4A and IL-2 killed EG7.ova better than the same effectors generated with EG7.ova plus IL-2 alone, but the difference does not appear to be significant. However, when the cell counts were taken, the culture with LmeIF4A produced 2.5-fold higher cells than the cultures without LmeIF4A. These results, shown below in Table 4, are expressed in lytic units per culture, and demonstrate overall strength of LmeIF4A to expand specific CTL numbers in vitro.

TABLE IV

Recovery of Mononuclear Cells from LmeIF4A Containing Cultures

| Immunized With | In Vitro Stimulated With | No. of Cells ($10^6$) Recovered/$10^6$ Mononuclear Cells Added | Total Lytic Units (LU50)/ Culture |
|---|---|---|---|
| Ova/PLGA sm Nr | EG7.Ova plus IL-2 | 6.4 | 75.2 |
| | EG7.Ova plus IL-2 and LmeIF4A | 16 | 388.8 |

Example 16

Augmentation of the Induction of Alloreactive CTL by LmeIF4A

This examples illustrates the induction of murine alloreactive CTL by LmeIF4A.

Figure 18:
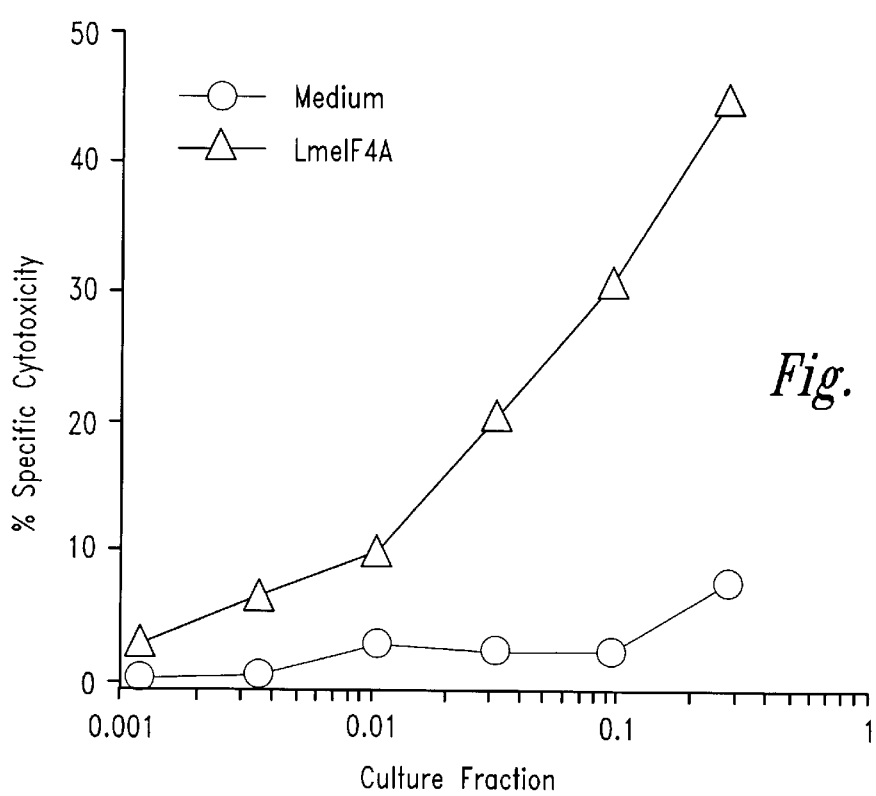
FIG. 18 illustrates the induction of murine alloreactive CTL by an LmeIF4A polypeptide.

$2.5 \times 10^6$ BALB/c spleen cells were cultured with $5 \times 10^6$ irradiated (3500 R) C57BL/6 spleen cells in 2 ml of RPMI:FCS in the presence or absence of 10 µg/ml gel-purified LmeIF4A. Cultures were harvested on day 5, washed and tested at different effector cell concentrations (culture fraction) for cytolytic activity against $^{51}$Cr labelled EL4 cells (2,000/well) in a 4 hr release assay in 200 µl cultures. Data are expressed, in FIG. 18, as percent specific release, which is calculated as:

$$\frac{100 \times (CPM \text{ experimental}) - (CPM \text{ spontaneous})}{(CPM \text{ maximum}) - (CPM \text{ spontaneous})}$$

These results indicate that LmeIF4A is capable of significantly enhancing alloreactive CTL. Taken together with the other results described above, the Leishmania eIF4A homologue appears to have potent adjuvant activity in a variety of assay systems. Furthermore, its ability to induce IL-12, together with its lack of toxicity, makes it a unique adjuvant.'

Example 17

Tumor Regression After Administration of LmeIF4A and Antigen

Female C57BL/6 (H-$2^b$) mice of 6–8 weeks of age were immunized once with a subcutaneous injection with 50 µg LmeIF4A either alone or 30 µg encapsulated in poly-lactide-glycolide beads (LbeIF/PLG), VSV peptides alone or in PLG beads, GM-CSF in PLG beads, or vehicle (PBS). N1 cells were generated from the EL4 cell by transfection of the VSV (vesicular stomatitis virus) nucleocapsid protein gene. Because the plasmid directing expression of the VSV nucleocapsid protein contains the neomycin resistance gene as a selectable marker, the cell line was maintained in a selective medium containing G418. Recombinant LmeIF4A was produced from E. coli transfectants and purified by HPLC fractionation. N1-specific peptide antigen was chemically synthesized and also purified by HPLC. Proteins were encapsulated into PLG microspheres by Southern Research Institute (Birmingham, Ala.).

Approximately $2 \times 10^5$ N1 cells were inoculated intradermally into the right flank of C57BL/6 mice. After palpable tumors were established, mice were randomized into groups of five and given subcutaneous injections of the various peptides listed above on the opposite flank. Tumor growth was monitored by measuring the diameters of tumors every 2 or 3 days and converting the measurement into volume according to the formula $V=4/3 \pi r^3$.

Figure 19:
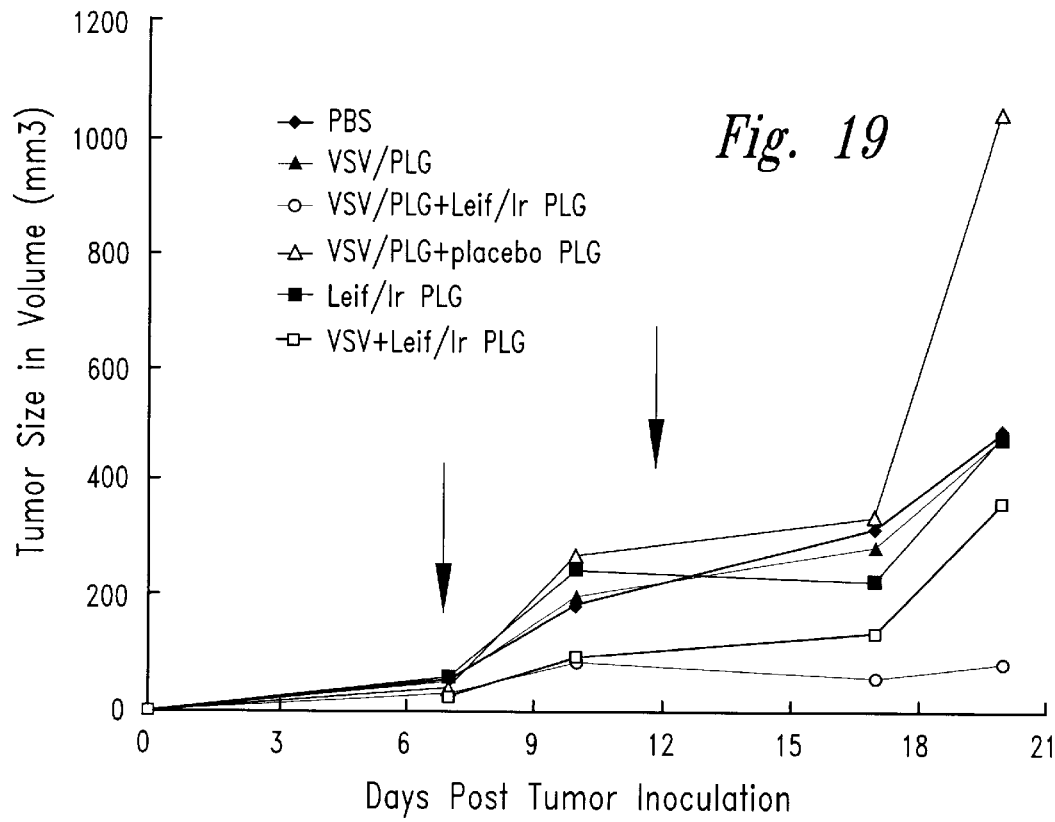
FIG. 19 shows tumor regression following administration of tumor antigen and LmeIF4A polypeptide contained in microspheres.
Figure 20:
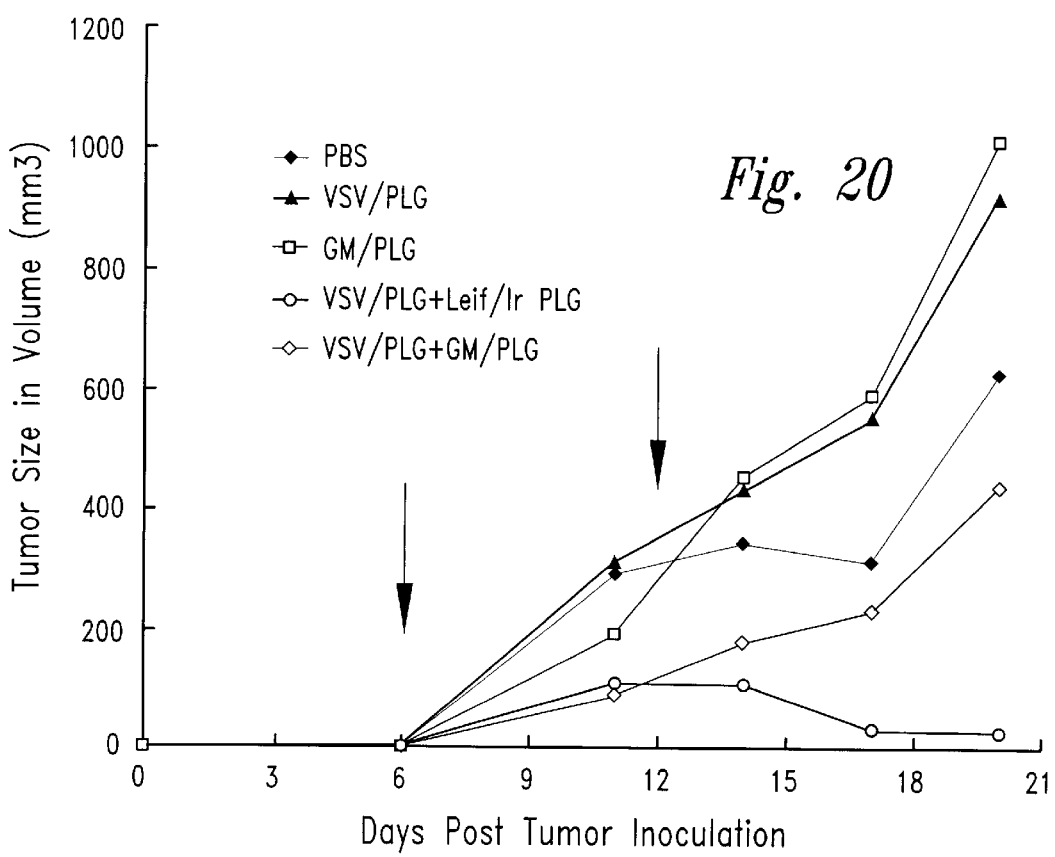
FIG. 20 shows tumor regression following administration of tumor antigen and LmeIF4A polypeptide contained in microspheres.

The efficacy of LmeIF4A in eliciting immune responses against tumor specific antigens was tested. In the murine tumor N1, the octameric antigenic peptide epitope RGYVYQGL (SEQ ID NO:15) is constitutively presented by the H-$2K^b$ molecule. As shown in FIG. 19, the injected combination of VSV/PLG and LmeIF4A/PLG resulted in significant suppression of tumor growth. Regression was not observed in the control mice or in mice receiving other combinations of antigens. A second study (FIG. 20) confirmed this result and also demonstrated that LmeIF4A is a much better adjuvant than GM-CSF. In this experiment, tumors started to regress one week after antigen injection in mice administered with the tumor specific VSV/PLG and LmeIF4A/PLG. Indeed, three out of five mice completely rejected their tumors in this particular study. In addition, soluble LeIF also had potent anti-tumor activity in combination with PLG encapsulated VSV peptide (FIG. 21).

In addition, the immune response generated through LmeIF4A and tumor antigen co-immunization was highly specific. The residual tumor mass in mice who did not completely reject N1 tumor was surgically removed. When these tumor cells were cultured in medium containing 0.2 mg/ml G418, they were killed two days later. In contrast, original N1 cells used in the tumor inoculum were resistant to G418. Thus, the residual tumor was derived from N1 mutants that had lost the expression plasmid containing both the antigenic VSV sequence and the neomycin resistance genes. Therefore, LeIF is capable of boosting specific immune response against a predefined antigen, which, in turn, can lead to a therapeutic effect against tumors.

Example 18

Treatment of Established Tumors with LmeIF

Female C57BL/6 mice were injected s.c. with $2 \times 10^5$ Lewis lung carcinoma cells. By eight days following injection, tumors were detected in all mice. Mice were then divided into two groups of five mice each. On days 8, 10, 13, and 16 after tumor inoculation, mice were injected s.c., at a site distant from the tumor, with 0.2 ml saline or 50 µg LmeIF in 0.2 ml saline. Tumor growth was measured on days 8, 10, 13, and 16. As shown in the following table, mice receiving LmeIF had substantially reduced tumor growth by day 16.

TABLE V

Inhibition of Tumor Growth by LmeIF

| Group | Average tumor volume in mm$^3$ | | | |
|---|---|---|---|---|
| | day 8 | day 10 | day 13 | day 16 |
| Saline injected | 5.21 | 12.61 | 41.06 | 283.53 |
| Lmeif injected | 6.79 | 10.83 | 26.75 | 69.48 |

From the foregoing, it will be appreciated that, although specific embodiments of the invention have been described herein for the purpose of illustration, various modifications may be made without deviating from the spirit and scope of the invention.

We claim:

1. A method of enhancing or eliciting an immune response to an antigen in a patient, comprising administering to a patient an antigen and an LmeIF4A polypeptide comprising an amino acid sequence encoded by a DNA sequence selected from the group consisting of:

(a) nucleotides 117 through 1325 of SEQ ID NO:3; and (b) DNA sequences that hybridize to a nucleotide sequence complementary to nucleotides 117 through 1325 of SEQ ID NO: 3 under moderately stringent conditions, wherein the moderately stringent conditions comprise prewashing in a solution of 5×SSC, 0.5% SDS, 1.0 mM EDTA (pH 8.0), hybridizing at 50° C.–65° C. 5×SSC overnight, followed by washing twice at 65° C., for 20 minutes with each of 2×, 0.5× and 0.2×SSC containing 0.1% SDS, and wherein the DNA sequence encodes a polypeptide that stimulates a Th1 immune response in peripheral blood mononuclear cells obtained from a Leishmania-infected individual.

2. The method of claim 1 wherein the LmeIF4A polypeptide comprises amino acids 49–403 of SEQ ID NO:4.

3. The method of claim 1 wherein the LmeIF4A polypeptide comprises amino acids 1–403 of SEQ ID NO:4 or a portion thereof.

4. The method of claim 1 wherein the LmeIF4A polypeptide additionally comprises an immunoglobulin Fc region.

5. A method of enhancing or eliciting an immune response to an antigen in a patient, comprising administering to a patient an antigen and an LmeIF4A polypeptide comprising amino acids 1–403 of SEQ ID NO: 4, or a variant thereof that differs only in conservative substitutions or modifications.

6. The method of any of claims 1–4 and 5, wherein the antigen and the LmeIF4A polypeptide are present in the same composition.

7. The method of any of claims 1–4 and 5 wherein the antigen is encapsulated in biodegradable microspheres.

8. The method of any of claims 1–4 and 5 wherein the LmeIF4A polypeptide is encapsulated in or associated with the surface of biodegradable microspheres.

9. The method of any of claims 1–4 and 5 wherein the antigen and the LmeIF4A polypeptide are encapsulated in biodegradable microspheres.

10. The method of any of claims 1–4 and 5 wherein the antigen and the LmeIF4A polypeptide are administered at different times.

* * * * *